(12) United States Patent
Tal et al.

(10) Patent No.: US 8,657,790 B2
(45) Date of Patent: Feb. 25, 2014

(54) ACCESS DEVICE WITH BLUNTING DEVICE

(75) Inventors: Michael Tal, Woodbridge, CT (US);
John P. Marano, Jr., Madison, CT (US);
James R. Flom, San Mateo, CA (US);
John F. Lapetina, San Francisco, CA (US); Robert Yuen Lee Ang, New York, NY (US); Aaron Abroff, San Carlos, CA (US); Carl Gandarillas, Beacon Falls, CT (US); Michael F. Wei, Redwood City, CA (US); Joshua Druker, San Francisco, CA (US); Janelle Anderson, New York, NY (US)

(73) Assignee: Access Scientific, Inc., San Diego, CA (US)

(*) Notice: Subject to any disclaimer, the term of this patent is extended or adjusted under 35 U.S.C. 154(b) by 2 days.

(21) Appl. No.: 13/283,325

(22) Filed: Oct. 27, 2011

(65) Prior Publication Data

US 2012/0041371 A1 Feb. 16, 2012

Related U.S. Application Data

(63) Continuation of application No. 11/910,223, filed as application No. PCT/US2006/011624 on Mar. 30, 2006, now abandoned.

(60) Provisional application No. 60/666,547, filed on Mar. 30, 2005, provisional application No. 60/743,285, filed on Feb. 14, 2006.

(51) Int. Cl.
*A61M 5/178* (2006.01)

(52) U.S. Cl.
USPC .................................................. 604/164.08

(58) Field of Classification Search
USPC .................................................. 604/164.08
See application file for complete search history.

(56) References Cited

U.S. PATENT DOCUMENTS

| | | |
|---|---|---|
| 3,565,074 A | 2/1971 | Foti et al. |
| 4,068,659 A | 1/1978 | Moorehead |
| 4,205,675 A | 6/1980 | Vaillancourt |
| 4,230,123 A | 10/1980 | Hawkins, Jr. |
| 4,417,886 A | 11/1983 | Frankhouser et al. |
| 4,525,157 A | 6/1985 | Vaillancourt |
| 4,581,019 A | 4/1986 | Curelaru et al. |
| 4,629,450 A | 12/1986 | Suzuki et al. |
| 4,655,750 A | 4/1987 | Vaillancourt |
| 4,661,300 A | 4/1987 | Daugherty |
| 4,791,937 A | 12/1988 | Wang |

(Continued)

FOREIGN PATENT DOCUMENTS

| | | |
|---|---|---|
| EP | 0139091 | 7/1984 |
| EP | 0161636 | 11/1985 |

(Continued)

OTHER PUBLICATIONS

A photograph of various access devices.

(Continued)

*Primary Examiner* — Jason Flick
(74) *Attorney, Agent, or Firm* — Knobbe Martens Olson & Bear LLP

(57) ABSTRACT

A device may include a hollow needle, a dilator mounted coaxially on the needle, and a sheath mounted coaxially on the dilator. The dilator may be slideably displaceable relative to the sheath.

16 Claims, 44 Drawing Sheets

(56) References Cited

U.S. PATENT DOCUMENTS

| | | | |
|---|---|---|---|
| 4,850,975 | A | 7/1989 | Furukawa |
| 4,869,259 | A | 9/1989 | Elkins |
| 4,894,052 | A | 1/1990 | Crawford |
| 4,961,729 | A | 10/1990 | Vaillancourt |
| 4,978,334 | A | 12/1990 | Toye et al. |
| 5,066,284 | A | 11/1991 | Mersch et al. |
| 5,108,374 | A | 4/1992 | Lemieux |
| 5,171,218 | A | 12/1992 | Fonger et al. |
| 5,242,410 | A | 9/1993 | Melker |
| 5,246,426 | A | 9/1993 | Lewis et al. |
| 5,250,038 | A | 10/1993 | Melker et al. |
| 5,295,969 | A | 3/1994 | Fischell |
| 5,295,970 | A | 3/1994 | Clinton et al. |
| 5,306,253 | A | 4/1994 | Brimhall |
| 5,312,355 | A | 5/1994 | Lee |
| 5,330,433 | A | 7/1994 | Fonger et al. |
| 5,366,441 | A | 11/1994 | Crawford |
| 5,380,290 | A | 1/1995 | Makower et al. |
| 5,419,766 | A | 5/1995 | Chang et al. |
| 5,512,052 | A | 4/1996 | Jesch |
| 5,542,932 | A | 8/1996 | Daugherty |
| 5,589,120 | A | 12/1996 | Khan et al. |
| 5,676,689 | A | 10/1997 | Kensey et al. |
| 5,688,249 | A | 11/1997 | Chang et al. |
| 5,704,914 | A * | 1/1998 | Stocking et al. ......... 604/164.07 |
| 5,749,857 | A | 5/1998 | Cuppy |
| 5,795,339 | A | 8/1998 | Erskine |
| 5,810,780 | A | 9/1998 | Brimhall et al. |
| 5,820,596 | A | 10/1998 | Rosen et al. |
| 5,827,202 | A | 10/1998 | Miraki et al. |
| 5,830,190 | A | 11/1998 | Howell |
| 5,833,662 | A | 11/1998 | Stevens |
| 5,858,002 | A | 1/1999 | Jesch |
| 5,885,253 | A | 3/1999 | Liu |
| 5,910,132 | A | 6/1999 | Schultz |
| 5,935,110 | A | 8/1999 | Brimhall |
| 6,046,143 | A | 4/2000 | Khan et al. |
| 6,074,377 | A | 6/2000 | Sanfilippo |
| 6,080,141 | A | 6/2000 | Castro et al. |
| 6,117,108 | A * | 9/2000 | Woehr et al. ................. 604/110 |
| 6,120,494 | A | 9/2000 | Jonkman |
| 6,179,813 | B1 | 1/2001 | Ballow et al. |
| 6,277,100 | B1 | 8/2001 | Raulerson et al. |
| 6,287,278 | B1 | 9/2001 | Woehr et al. |
| 6,436,070 | B1 | 8/2002 | Botich et al. |
| 6,461,362 | B1 | 10/2002 | Halseth et al. |
| 6,524,277 | B1 | 2/2003 | Chang |
| 6,607,511 | B2 | 8/2003 | Halseth et al. |
| 6,692,462 | B2 | 2/2004 | Mackenzie et al. |
| 6,726,659 | B2 | 4/2004 | Stocking et al. |
| 6,808,520 | B1 | 10/2004 | Fourkas et al. |
| 6,994,693 | B2 | 2/2006 | Tal |
| 7,001,396 | B2 | 2/2006 | Glazier et al. |
| 7,025,746 | B2 | 4/2006 | Tal |
| 7,192,433 | B2 | 3/2007 | Osypka et al. |
| 7,270,649 | B2 | 9/2007 | Fitzgerald |
| 7,556,617 | B2 | 7/2009 | Voorhees, Jr. et al. |
| 7,722,567 | B2 | 5/2010 | Tal |
| 7,922,696 | B2 | 4/2011 | Tal et al. |
| 2002/0072712 | A1 | 6/2002 | Nool et al. |
| 2004/0092879 | A1 | 5/2004 | Kraus et al. |
| 2004/0171988 | A1 | 9/2004 | Moretti |
| 2006/0129100 | A1 | 6/2006 | Tal |
| 2008/0262430 | A1 | 10/2008 | Anderson et al. |
| 2008/0262431 | A1 | 10/2008 | Anderson et al. |
| 2009/0221961 | A1 | 9/2009 | Tal et al. |
| 2011/0009827 | A1 | 1/2011 | Bierman et al. |
| 2011/0021994 | A1 | 1/2011 | Anderson et al. |
| 2011/0202006 | A1 | 8/2011 | Bierman et al. |
| 2011/0218496 | A1 | 9/2011 | Bierman |
| 2011/0276002 | A1 | 11/2011 | Bierman |
| 2012/0065590 | A1 | 3/2012 | Bierman et al. |

FOREIGN PATENT DOCUMENTS

| | | |
|---|---|---|
| EP | 0806221 | 11/1985 |
| EP | 0 352 928 | 1/1990 |
| EP | 0502714 | 11/1995 |
| EP | 0734739 | 10/1996 |
| JP | 11299897 | 11/1999 |
| JP | 2001-190682 | 7/2001 |
| JP | 2003/265615 | 9/2003 |
| KR | 20050027359 | 3/2005 |
| WO | WO 83/01575 | 5/1983 |
| WO | WO 94/12233 | 6/1994 |
| WO | WO 01/23028 | 4/2001 |
| WO | WO 03/057272 | 7/2003 |
| WO | WO 2008/131289 | 10/2008 |
| WO | WO 2010/048449 | 4/2010 |
| WO | WO 2010/056906 | 5/2010 |
| WO | WO 2010/083467 | 7/2010 |
| WO | WO 2010/132608 | 11/2010 |
| WO | WO 2011/097639 | 8/2011 |

OTHER PUBLICATIONS

Arrow Trauma Products No. TRM-C 12/00 11M, Arrow International, dated 2000.

Australian Patent Application Office Action, 2006302805 dated Dec. 6, 2010.

European Search Report and Written Opinion, EP 11 00 4964 Dated Aug. 4, 2011.

Japanese Office Action for Application No. 2008-504351, dispatch date Jul. 22, 2010.

Japanese Office Action for Application No. 2008-504351, dispatch date Mar. 2, 2011.

Photos of a peripheral emergency infusion device Applicant believes to be produced by Arrow International Inc.

Photos of a splittable catheter design.

Photos of an infusion device Applicant believes to be produced by B. Braun Medical Inc.

Supplemental European Search Report for PCT/US2006011624 dated Mar. 3, 2009.

* cited by examiner

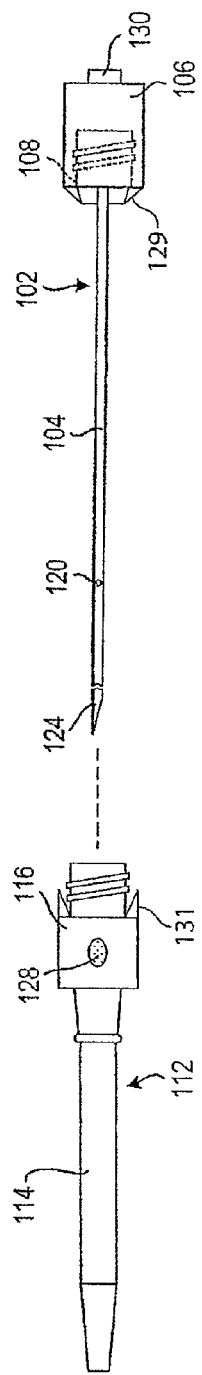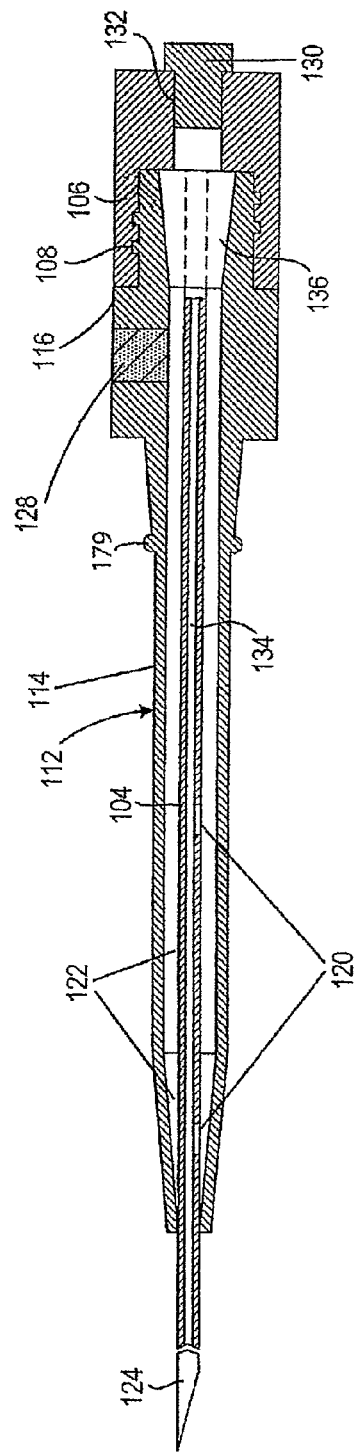

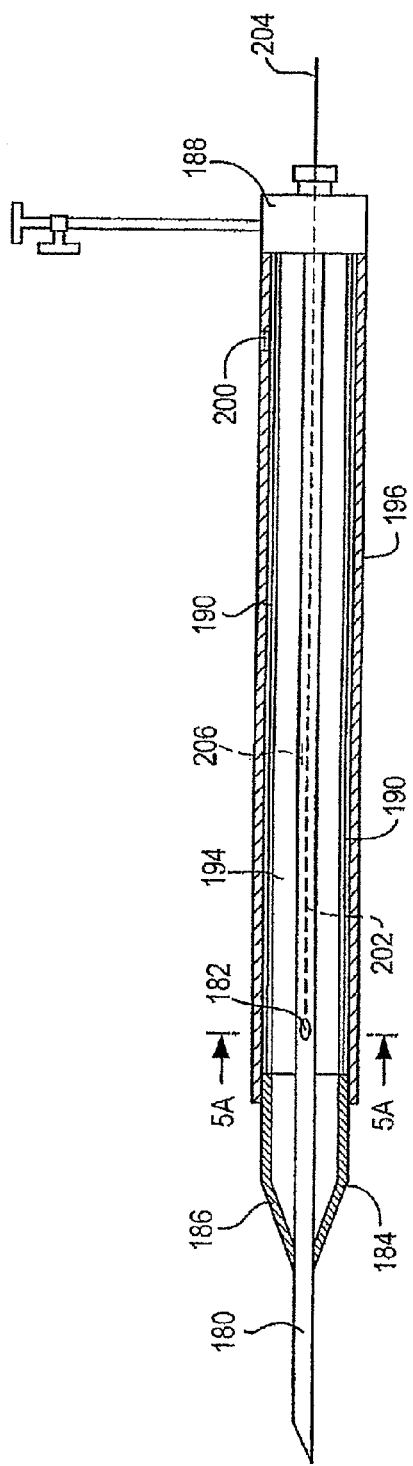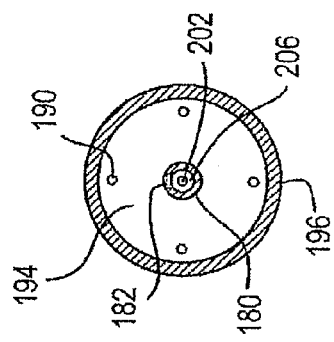

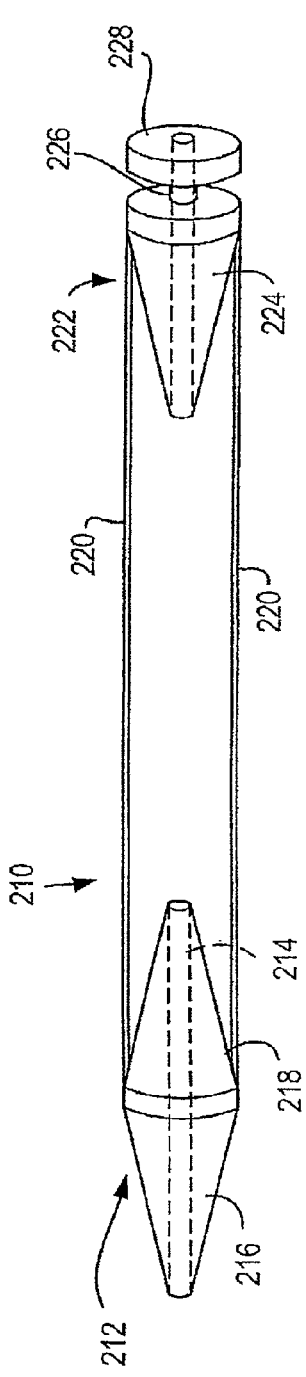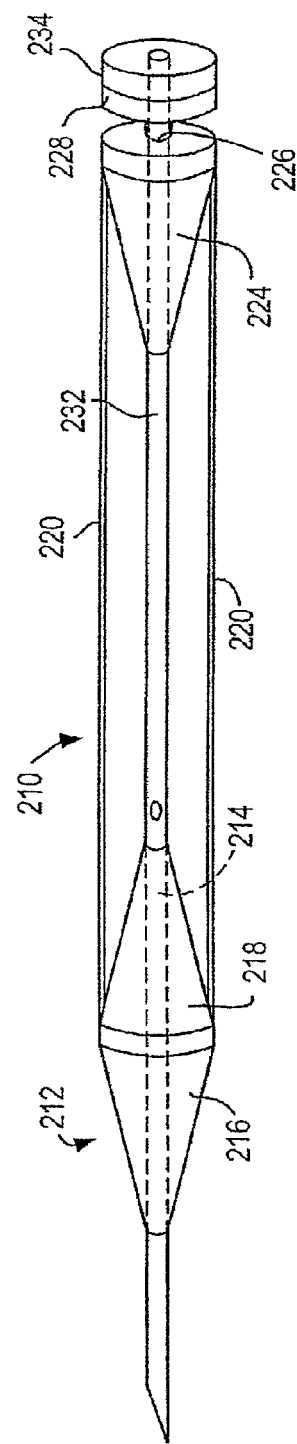

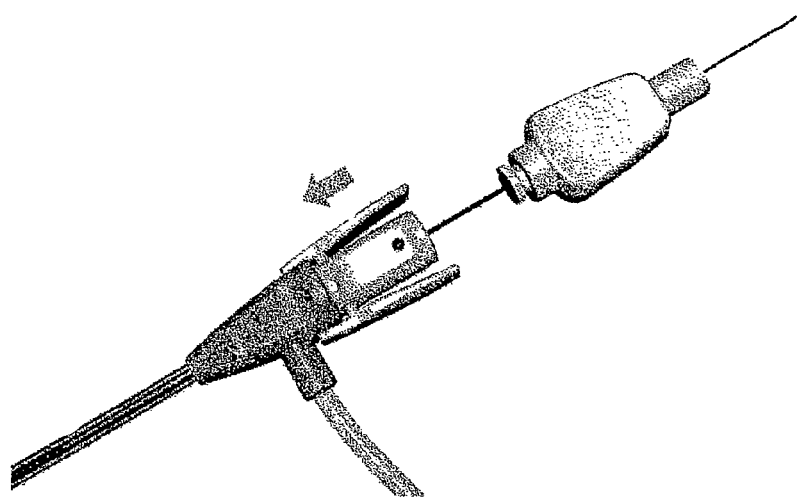
Fig. 62
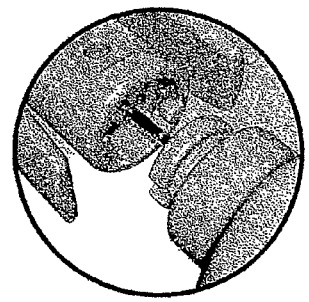
Fig. 63
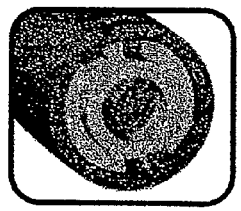 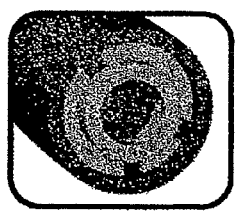 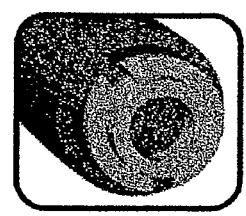
Fig. 64   Fig. 65   Fig. 66

ACCESS DEVICE WITH BLUNTING DEVICE

CROSS-REFERENCE TO RELATED APPLICATIONS

This application is a continuation under 35 U.S.C. §120 of U.S. patent application Ser. No. 11/910,223 (filed 19 Jun. 2008), which claims the benefit of International Appl. No. PCT/US2006/011624 (filed 30 Mar. 2006), which was published in English and designated the United States of America, and which further claims the benefit under 35 U.S.C. §119(e) to U.S. Provisional Patent Application Ser. Nos. 60/666,547 (filed 30 Mar. 2005) and 60/743,285 (filed 14 Feb. 2006), the entirety of which is hereby expressly incorporated by reference herein.

BACKGROUND

A preferred non-surgical method for inserting a catheter or vascular sheath into a blood vessel involves the use of the Seldinger technique, which includes an access needle that is inserted into a patient's blood vessel. A guidewire is inserted through the needle and into the vessel. The needle is removed, and a dilator and sheath combination are then inserted over the guidewire. The dilator and sheath combination is then inserted a short distance through the tissue into the vessel, after which the dilator is removed and discarded. The catheter is then inserted through the sheath into the vessel to a desired location.

Alternatively, with microaccess techniques an access needle is inserted into a patient's blood vessel. A guidewire is inserted through the needle and into the vessel. The needle is removed, and a dilator is then inserted over the guidewire. The dilator combination is then inserted a short distance through the tissue into the vessel, after which the guidewire is removed and discarded. The dilator is left in place, and a separate sheath kit is used. A larger guidewire is inserted into the dilator and the dilator is removed. A dilator and sheath combination is inserted. Then the dilator and guidewire are removed. The catheter is then inserted through the sheath into the vessel to a desired location.

A number of vascular access devices are known. See, for example, U.S. Pat. Nos. 4,581,019, 4,629,450, 4,772,264, 4,978,334, 5,158,544, 5,424,410, 5,312,355, 5,512,052, 5,728,132, 5,885,217, 5,919,160, 6,120,494, 6,179,823, and 6,210,366, each of which is incorporated herein by reference, wherein various devices for vascular access are described. However, none of these devices has the ease and safety of use that physicians would prefer, and there is thus a need for an easier-to-use and safer vascular access device, especially one that would clearly indicate when a blood vessel has been punctured.

SUMMARY

Preassembled vascular access devices may include a hollow needle, a dilator coaxially disposed on at least a portion of the needle, and a sheath coaxially mounted on at least a portion of the dilator. Spaces may be defined between the needle and dilator and between the dilator and the sheath. The hollow needle bore may communicate with one or more of the spaces through apertures defined in the needle and/or dilator. The sheath may be translucent or transparent, thereby allowing a user to see a blood flash and confirm that vascular access is achieved.

BRIEF DESCRIPTION OF THE DRAWINGS

FIGS. 1 and 2 are each a schematic representation of one embodiment of a vascular access device.

FIG. 5 is a partly cross-sectional view of a further embodiment.

FIG. 5A is a cross-section along line 5A-5A.

FIG. 6 is a partly cross-sectional view of another embodiment.

FIG. 7 is a partly cross-sectional view of yet another embodiment.

FIG. 39 depicts the components of FIGS. 37 and 38 assembled.

FIGS. 59-68 depict various views and operation of a further exemplary embodiment of a needle-dilator-sheath assembly.

DETAILED DESCRIPTION

Figure 3:
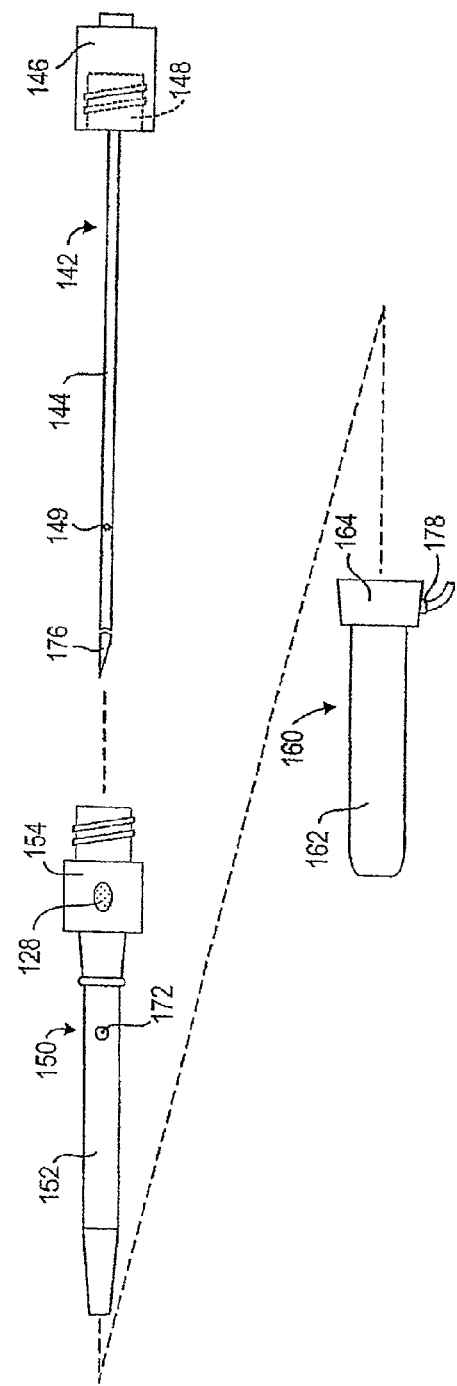
FIGS. 3 and 4 are each a schematic representation of another embodiment.

U.S. Patent Applications 60/343,814 and Ser. No. 10/329,173 describe vascular access devices and are hereby incorporated herein by reference.

In some embodiments, a dilator or a sheath and dilator are mounted on a needle, which needle has a lateral opening proximal to the needle distal tip. Prior to insertion, the needle is positioned so that the distal end of the needle is distal to the distal end of the dilator. After insertion of the needle into a blood vessel, the needle opening permits blood to flow into an annular space between the needle and the dilator to indicate that the distal end of the needle has punctured the blood vessel. Additionally or alternatively, blood flows into an annular space formed by the sheath to indicate that the blood vessel has been punctured. In addition, blood may flow to a transparent hub or an optional side port to provide further indication access has been achieved and to help the user to determine whether access has been gained to an artery or a vein.

Once vascular access is achieved, that is, once the distal tip of the needle punctures a blood vessel and blood flows through a lateral opening in the needle to one of the annular spaces described above and as appropriate, into a side port, a guidewire is advanced or threaded through the needle, and then the entire apparatus, including the needle, the dilator, and a sheath, can be advanced over the guidewire into the blood vessel. Alternatively the guidewire may be threaded through the needle, and then the dilator and sheath can be advanced off the needle, over the guidewire into the blood vessel. When the sheath is in position, the inner dilator, needle and guidewire can be removed together. Thus, the guidewire protects the needle tip, and the needle, with the guidewire in it, can then be bent for added safety, to prevent removal of the guidewire and consequential exposure of the needle tip. Alternatively, the guidewire can be left in place for catheter placement. In some embodiments, described in more detail below, the distal tip of the needle can be contained within the dilator, which also may contribute to safety.

In one embodiment, the dilator has a distal member that can be advanced distally or the distal tip of the needle can be retracted so that the distal tip of the dilator distal member extends distally over the distal tip of the needle. The dilator distal member then protects the blood vessel wall as the needle and dilator, or the needle, dilator, and sheath, or the dilator and sheath are advanced or withdrawn from a blood vessel, preferably over a guidewire. In addition, when the needle, dilator, and/or sheath are pulled out, the healthcare worker is protected.

In another embodiment, there is a coaxial dilator system, with an inner dilator and an outer dilator. The inner dilator can be advanced independently distally to the distal tip of the needle. The inner dilator then covers the needle tip, the inner dilator distal member then protects the blood vessel wall as the needle, dilator or the needle, dilator, sheath are advanced or withdrawn from a blood vessel, preferably over a guidewire. In addition, when the needle or needle, dilator, and/or sheath are pulled out, the worker is protected.

In another embodiment, the needle can be rotated relative to the dilator or the dilator and sheath, so that the needle tip, which is inserted into a blood vessel with the needle distal tip bevel up, can be rotated 180 degrees in the vessel so that the needle distal tip bevel is down. When the needle distal tip is in this position, it is less likely that movement of the needle distal tip will cause injury to the blood vessel. The proximate portion of the needle member may have color coding, words, or other indicia to indicate the relative position of the needle tip level. Also, the needle member proximal portion may have a notch, pivot, indent, or other mechanism to indicate relative position and/or to hold the needle member in position relative to the dilator or the dilator and sheath.

The disclosed vascular access devices have several uses, including access to every vessel when a vascular sheath is needed as in stent placement, percutaneous transluminal coronary angioplasty (PTCA), etc. or when a peel-away sheath is needed, for example, for inserting PICC lines, pacemaker leads, etc. In addition, the disclosed vascular access devices would be useful for access to dialysis grafts and fistulas, which are superficial structures and where access is sometimes needed quickly, especially during a de-clotting procedure. Another use would be for placement of central lines (femoral, subclavian or internal jugular). Instead of use of a large (18 G) needle (current technique), followed by advancement of a dilator over a guidewire and exchanging it for a triple lumen catheter or vascular sheath, a large needle or a small needle can be used to gain vascular access with a vascular sheath through which a triple lumen or any other catheter can be safely placed.

The disclosed vascular access devices may provide several advantages, the first of which is efficiency. Instead of the current multi-step access method with an exchange of guidewires and sheaths, these devices can reduce the number of steps and simplify access. Another advantage is safety. After a vessel is accessed, the guidewire can be left in to protect the needle tip. The needle, dilator and guidewire can be removed together after the sheath is in place. If no additional access is needed in the same procedure, the needle can be bent for added safety. This is contrary to the current technique where the unprotected bloody needle is removed from the guidewire after vascular access is gained. Alternatively, the guidewire can be left in place to provide further access through the sheath and the dilator distal member protects the distal tip of the needle and ultimately the user. Another advantage is the reduction of infection. By minimizing the number of guidewires and sheaths necessary to obtain vascular access, the opportunities for inadvertent contamination are decreased. A further advantage is that under non-hospital or field conditions, use of the disclosed devices will decrease the possibility of infection due to a non-sterile environment. A yet further advantage in some embodiments is the added stiffness of the system. The added stiffness provided by the needle may enable advancement of the system without multiple dilatations and thereby reduce trauma to the patient. In addition, the stiffness provided by the needle and/or other internal components permits the use of softer materials in forming the sheath, which may further reduce vascular trauma. For example, the sheath of a 6 French device can be made of a material having a hardness of about 55 durometer to about 75 durometer.

An even further advantage relates to the bleeding from the needle, the dilator, and around the wires that occurs during guidewire exchanges with current techniques. Such bleeding increases the spread of blood over the surgical field and the operator's gloves, thereby, increasing the chance of infection in case an inadvertent needle stick happens. The disclosed devices can decrease this risk of infection because the blood will flow into the sheath rather than into the surgical field as in the current technique.

Another and further advantage of some embodiments is that there is no need for over-the-wire exchanges. The device can be configured to eliminate the possibility of inadvertent guidewire misplacement into the vascular system during the access procedure. In the current technique, with exchange of the needle for a dilator and then for the sheath, it is a known complication that the operator fails to grasp the guidewire during those exchanges and the guidewire is inadvertently advanced with the dilator or catheter into the patient's vascular system. The guidewire then has to be removed either surgically or snared percutaneously.

Lastly, the present devices can be cost-effective because they may eliminate the need for an additional guidewire and coaxial dilator to be used in gaining vascular access.

In FIGS. 1 and 2, a needle section 102 includes a needle 104 and a proximal portion 106 with a twist lock member 108, and a dilator section 112 includes a dilator 114 and a hub 116. In one embodiment, needle 104 has one or more openings 120. Dilator 114 may be clear, semi-opaque, or translucent so that when blood flows into needle 104 and then through an opening 120 either (1) into an annular space 122 between needle 104 and dilator 114 or (2) into or through spaces (not shown) in dilator 114, the physician can see the blood. This will indicate to the physician that the distal end 124 of needle 104 has punctured a blood vessel (not shown). The ability to visualize a blood flash can provide other information as well. For example, the user can tell whether an artery or vein has been penetrated by the color of the blood (brighter red indicating arterial blood, darker red or purple indicating venous blood), the back pressure of the blood (higher pressure indicating arterial access, lower pressure indicating venous access), the speed at which the blood fills the device (slower filling being venous, faster filling being arterial) and whether the blood is pulsatile (pulsatile blood indicating arterial access, nonpulsatile blood indicating venous access).

As can be seen in FIG. 2, dilator hub 116 releasably engages needle proximal section 106. In some embodiments, the dilator hub can include a conical recess that receives a conical member forming a part of needle proximal section. Needle proximal section may include an annular portion having threading that engages reciprocal threading on the dilator hub. Other arrangements of threading, detents, or other snap- or force-fit configurations that achieve the same purpose of releasably engaging the proximal portions of the needle and dilator sections are also contemplated.

Hub 116 may optionally have a porous vent 128. Needle proximal portion 106 may optionally have a porous vent plug 130 that fits a channel 132 in fluid communication with lumen 134 of needle 104, the optional conical recess, and needle proximal portion 106 having lumen 136.

Needle proximal portion 106 may have color coding, words, or other indicia, such as a pivot or notch, to indicate to the operator the position of the bevel of distal tip 124 relative to dilator 114. Also, there may be a mechanical fit between dilator 114 and needle 104 so that the operator would sense by feel or sound when the needle has been rotated to change the position of the needle tip bevel.

Figure 4:
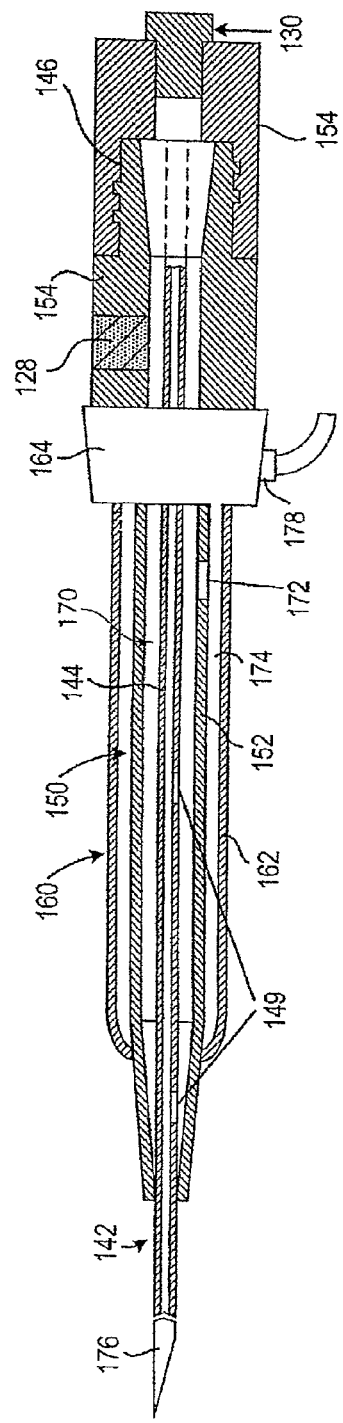

In the embodiment shown in FIGS. 3 and 4, a needle section 142 includes a needle 144 and a proximal portion 146 with a twist lock member 148, a dilator section 150 includes a dilator 152 and a hub 154, and a sheath section 160 includes a sheath 162 and a proximal portion 164. In one embodiment, needle 144 has one or more openings 149. Dilator 152 and sheath 162 may be clear, semi-opaque, or translucent so that when blood flows into needle 144 and then through opening 149 (1) into an annular space 170 between needle 144 and dilator 152, (2) into or through spaces (not shown) in dilator 152, or (3) through an opening 172 into an annular space 174 between dilator 152 and sheath 162, the physician can see the blood. As above, this will indicate to the physician that the distal end 176 of needle 144 has punctured a blood vessel (not shown). Dilator opening 172 may be positioned just proximal to needle aperture 149, or proximal to the transition from tube (or bullet) to conical tip. A dilator aperture 172 may also (or additionally) be positioned as proximal as possible yet still distal to seal 179. Alternatively, opening 172 may be positioned inside the sheath proximal to portion 164. Sheath proximal portion 164 may have a port 178 so that blood can be aspirated through a syringe (not shown). The sheath may contain a hemostatic valve (not shown) in the distal end 164 to prevent blood flow out the distal end of the sheath. The sheath proximal portion 164 is shown as having a frustoconical shape, but it may also have a distal cylindrical region shaped to receive a tube-like cover for packaging.

A drop of high-viscosity fluid may be placed in between the needle internal diameter and the guidewire at the needle proximal end. This can prevent the drawing of air into the device through the space between the needle and guidewire when blood is aspirated through the side port. Dow Corning 360 medical fluid, 12,500 cSt is an example fluid but other similar materials can be used. Rubber seals in the dilator hub can also help to seal the needle. The fluid drop and/or airtight seals are particularly useful when the device is being used to obtain venous access, because venous placement is often confirmed by aspiration. Aspiration is usually not necessary during arterial access, because the arterial blood pressure is sufficient to cause the blood to enter the device.

Proximal sections 108 and 116 and 146 and 154, respectively, may optionally have luer connecting members. For example, section 108 may have a male luer lock 129, and section 116 may have a female luer connector 131. Sections 146 and 154 may have comparable members, respectively.

As shown in FIG. 4 sections 142, 150, and 160 can be inserted into one another. Proximal sections 146, 154, 164 can twist or snugly fit together, such as with a luer connector, threading, a pressure or snap fit, a detent/groove arrangement, a post/hole arrangement, or a combination thereof. The structure shown in FIG. 2 is especially applicable here.

In another embodiment shown in a partial cross-section in FIG. 5, needle 180 has an opening or side hole 182. Dilator 184, which is arranged coaxially to needle 180, has a substantially hollow distal section 186 and a substantially solid proximal section 188, which sections 186 and 188 are connected by rigid or substantially rigid longitudinal members 190, to form an interrupted or discontinuous structure. The space between sections 186 and 188 not occupied by members 190 constitutes an annular or substantially annular space 194, into which blood can flow from opening 182. Sheath 196 is transparent or translucent, so that the blood in space 194 can be observed by the physician.

Dilator 184 may have one or more small openings, pores, or porous material 200, for example, in sheath 196, to allow air or gas to leave annular space 194 as blood enters. The openings themselves, or the openings in the porous material, are small enough that air will escape but blood will be retained. Suitable porous materials include a porous polymer such as self-sealing, white porous HDPE of pore size 2.5 microns.

The distal end 202 of a guidewire 204 may be preloaded, that is, positioned within a lumen 206 of needle 180. In this way blood will flow into needle 180 and out through opening 182, and not proximally out lumen 206. Once the physician sees the blood in annular space 194, guidewire 204 can be advanced distally through lumen 206 into a blood vessel (not shown). Another view of the relationship between needle 180, dilator longitudinal members 190, and sheath 196 can be seen in the cross-sectional view shown in FIG. 5A.

Separate configurations for a dilator member are shown in more detail in FIGS. 6 and 7. In FIG. 6, a dilator 210 shown has conical elements. A distal dilation section 212 includes a double cone design with a passageway 214 extending from the tip of one conical element 216 to the tip of another conical element 218. At least two stabilizing longitudinal members 220 extend from distal section 212 to a proximal section 222, which may include a single conical element 224 with a passageway 226 and a proximal twist or locking section 228.

The embodiment shown in FIG. 7 includes a dilator-needle combination where the dilator device described in FIG. 6 also includes a needle 232 that extends through passageway 214 to and through passageway 226. Needle 232 has a proximal section 234 that includes a twist or locking arrangement.

Figure 8:
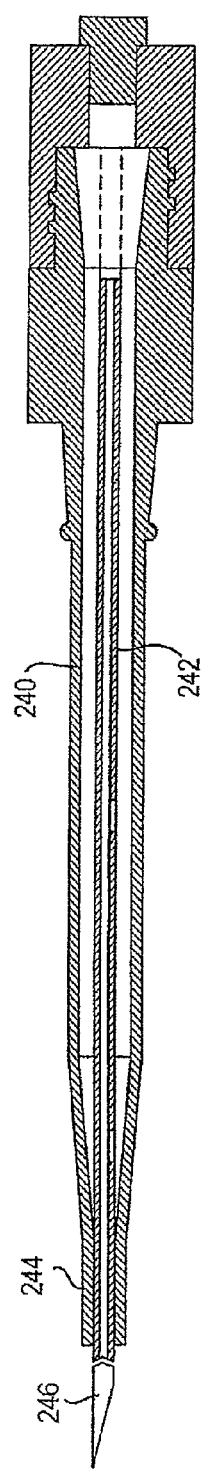
FIG. 8 is a partly cross-sectional view of an embodiment in which the distal portion of the dilator extends distally.
Figure 9A:
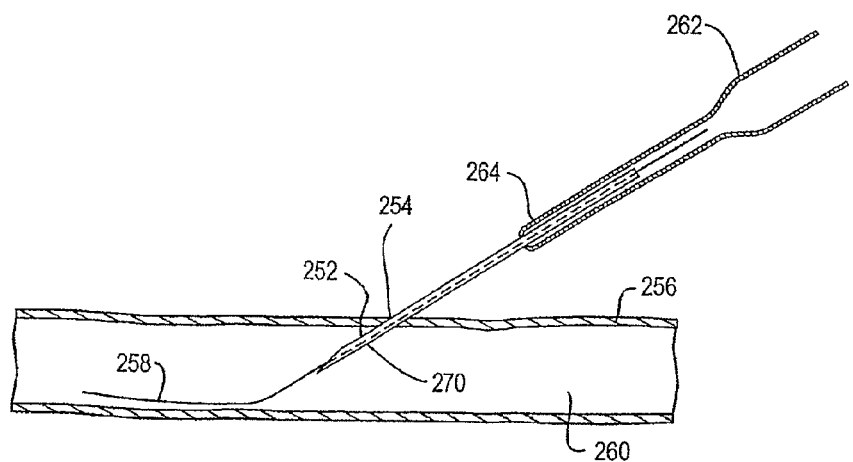
FIGS. 9A-C are schematic representations of use of the disclosed vascular access devices.
Figure 9B:
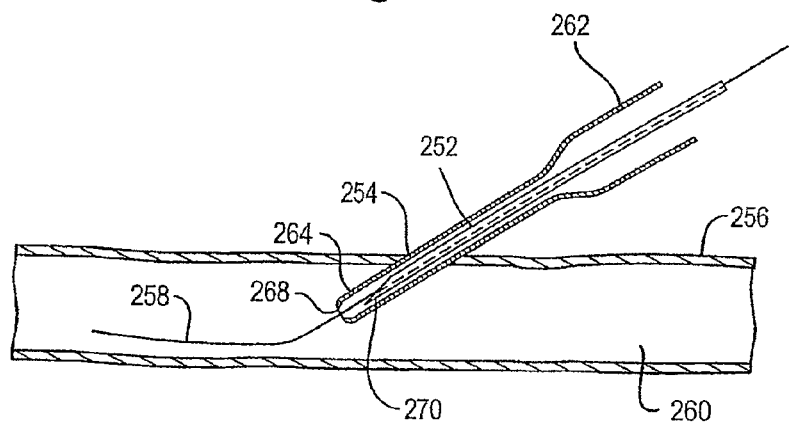
Figure 9C:
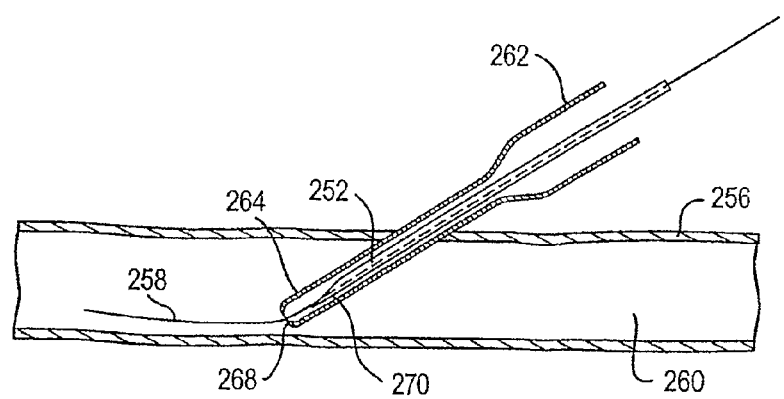

In the partial representation of an embodiment shown in FIG. 8, a dilator 240 is arranged circumferentially around a needle 242. Dilator 240 has a distal portion 244 that extends distally toward the distal tip 246 of needle 242. Alternatively, the inner, elongated dilator is coaxially located within the larger outer dilator. The inner elongated member can be advanced over the needle to dilate the vessel and/or protect the tip. As depicted in FIGS. 9A to 9C, a needle 252 is positioned in a puncture opening 254 in a blood vessel 256. A guidewire 258 extends distally from needle 252 into a lumen 260 of blood vessel 256. A dilator 262 positioned circumferentially around needle 252 has a distal portion 264. As shown in FIG. 9b, dilator distal portion 264 can be advanced over needle 252 so that the distal tip 268 of dilator distal portion 264 extends distally of the distal tip 270 of needle 252. Then, when, as shown in FIG. 9C, needle 252 and dilator 262 are advanced distally over guidewire 258, needle distal tip 270 is protected by dilator distal portion 264.

Figure 10A:
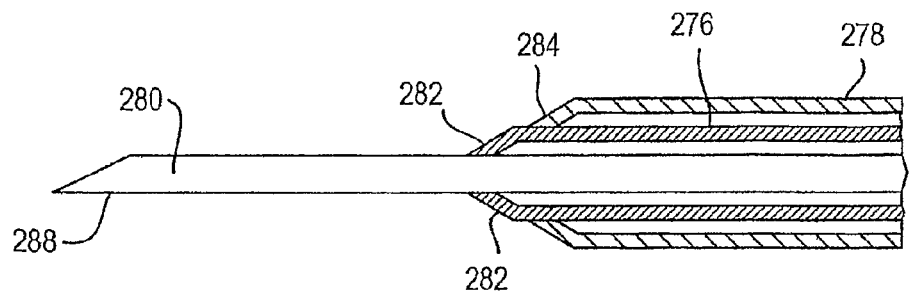
FIGS. 10A-B are schematic representations of an embodiment having a coaxial dilator system.
Figure 10B:
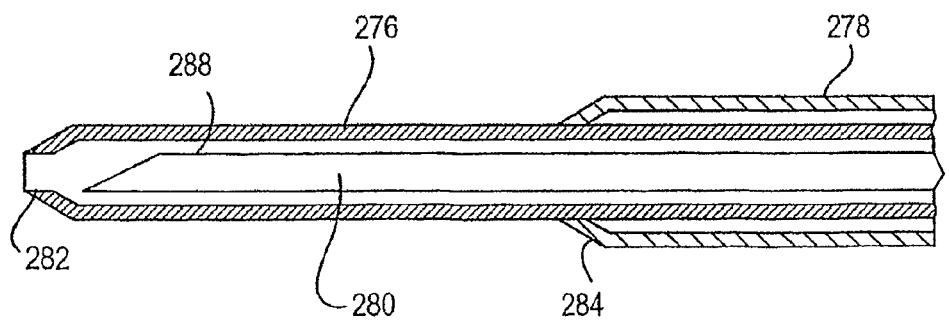

The embodiment shown in FIGS. 10A and 10B includes a coaxial dilator system including inner dilator 276 and outer dilator 278. Dilators 276 and 278 are arranged around needle 280, and the distal end 282 of inner dilator 276 is initially slightly distal of the distal end 284 of outer dilator 278. The proximal end (not shown) of inner dilator 276 is advanced distally to cause inner dilation distal end 282 to cover the distal end 288 of needle 280. Dilators 276 and 278 may interact or be held so that they retain their relative positions with regard to each other and needle 280 as the needle, dilator or needle, dilator, sheath combination is advanced into or withdrawn from a blood vessel (not shown), optimally over a guidewire (not shown).

Figure 11:
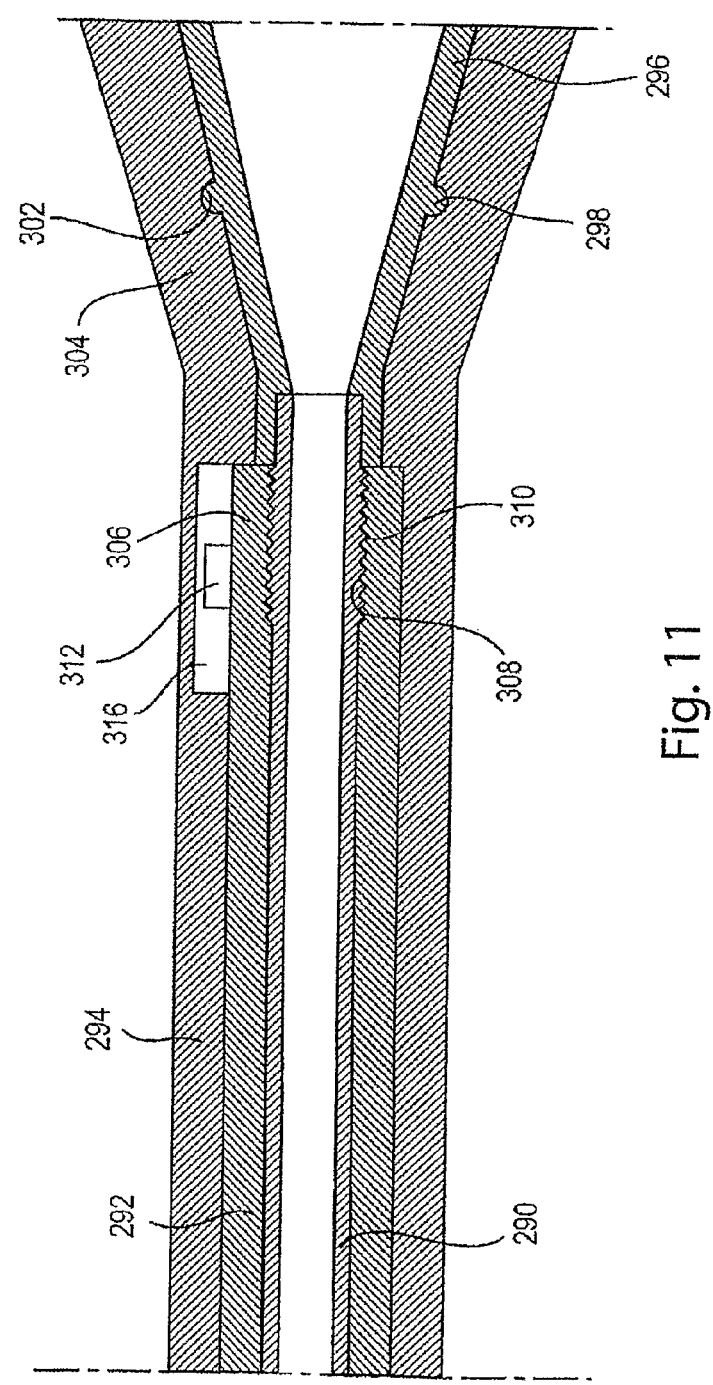
FIG. 11 is a schematic cross-sectional view of the proximal portion of the system of FIGS. 10A-B.

The coaxial dilator system shown in FIGS. 10A and 10B requires an activation system that causes one dilator to move in relation to the other dilator. It is preferred that the inner dilator would be advanced distally to cover the distal end of the needle while the outer dilator remains constant, or in place. The dilator system may be configured so that the outer dilator would remain relatively, substantially in place while the inner dilator is pushed, pulled, or slid in the distal direction. In the embodiment shown in FIG. 11, a proximal needle section 290 is circumferentially surrounded by a proximal inner dilator section 292 and an outer dilator section 294. Tapered needle hub 296 has at least one annular projection or ring 298 that is received in an annular groove 302 in the tapered outer dilator proximal hub 304. Inner dilator hub 306 has threading 308 that engages reciprocal threading 310 on needle 290 or on a separate needle member attached to needle 290 or needle hub 296. Inner dilator hub 304 has a projection or wing 312 that moves within, and is guided by, a slot 316 that prevents rotation of inner dilator 292 with respect to outer dilator 294. It is contemplated that other mechanical arrangements known or discernible to those skilled in the art would be acceptable, so long as they permitted advancement of the distal portion of the inner dilator over the distal portion of the needle without rotation of the inner dilator relative to the outer dilator.

In some embodiments, an access device may include a guidewire preloaded or preloadable in a needle and a dilator preloaded or preloadable in a sheath. The device may be provided as a kit in various stages of assembly. For example, a kit may include separate needle, guidewire, dilator, and sheath. The guidewire may be preloaded in the needle. The sheath may be preloaded on the dilator. The sheath and dilator may be preloaded on the needle. The sheath, dilator, and needle may be preloaded on the guidewire. The guidewire may be preloaded in the needle and provided with a separate sheath preloaded on a dilator. The dilator, needle, and guidewire may be preassembled and provided with a separate sheath.

In one embodiment, access may be obtained as follows: a needle is advanced into a vessel. When access is achieved, a guidewire (either preloaded in the needle or now introduced) is advanced into the vessel. The needle is then removed or partly retracted, and a dilator (with or without preloaded sheath) is advanced over the guidewire into the vessel. If the dilator is preloaded with a sheath, the dilator (and optionally the wire) are then removed, leaving the sheath in place. If the dilator is not preloaded with a sheath, then the dilator is removed, and a sheath is advanced over the guidewire into the vessel.

Figure 12:
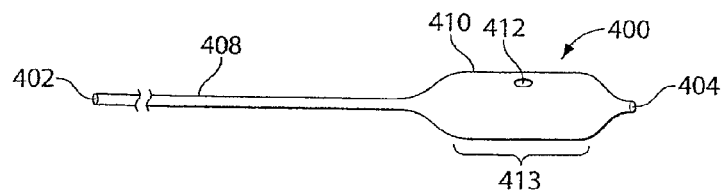
FIGS. 12 and 12A depict embodiments of dilators.

FIG. 12 depicts an alternate embodiment of a dilator 400. The dilator may be of unitary construction. It may include a bulging portion (or "bullet") 410 at its distal end 404; this portion performs the actual dilating. The distal end is tapered, such as with the illustrated frustoconical shape, to reduce tissue trauma during insertion. The bullet may include an aperture 412 to allow blood to pass from the needle (not shown), through the bullet, and into the sheath. The rest of the dilator, extending to the proximal end 402, may be a narrow-diameter spine 408. This configuration may be preferred because only the forward portion of the dilator is necessary to perform dilation; reducing the proximal diameter increases the volume of the sheath in that region and can improve visibility of the blood flash and reduce clotting. The bulging portion of the dilator may have a cylindrical region 413 of approximately or exactly constant diameter to facilitate sealing of a sheath taper against the cylindrical region.

Figure 12A:
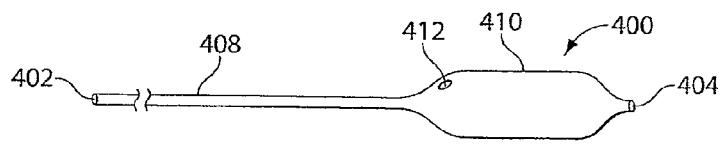

FIG. 12A depicts an alternate embodiment of a dilator 400 in which aperture 412 is positioned in the proximal transition of the bulging portion.

Figure 13:
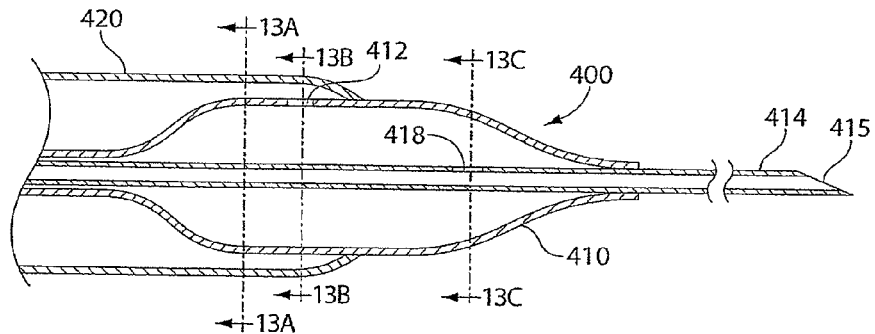
FIG. 13 depicts a longitudinal cross-section of an embodiment of a needle-dilator-sheath assembly.
Figure 13A:
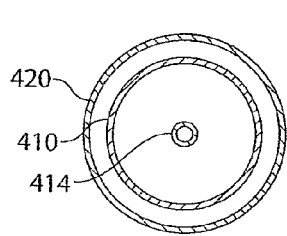
FIGS. 13A-C depicts the transverse cross-sections indicated in FIG. 13.
Figure 13B:
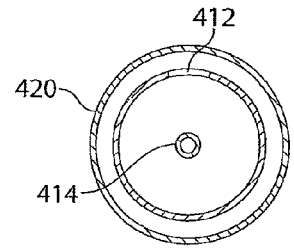
Figure 13C:
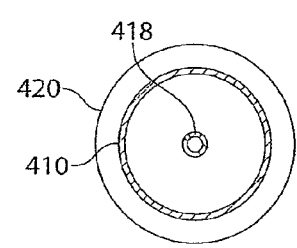

This arrangement may be better appreciated in FIG. 13, which shows an exemplary arrangement of needle 414, dilator 400, and sheath 420. Blood entering the tip 415 of the needle travels through the needle, emerges into the bullet through needle aperture 418, and then passes into the sheath space through dilator aperture 412. FIGS. 13A-C show the indicated transverse cross-sections of the FIG. 13 embodiment to illustrate better the spatial relationships. The spine may be so sized as not to define substantial volume between the spine and the needle; in this case, little or no blood flows between the spine and the needle proximal to aperture 412 because the spine does not contribute substantially to the space between the dilator and the needle.

Figure 15:
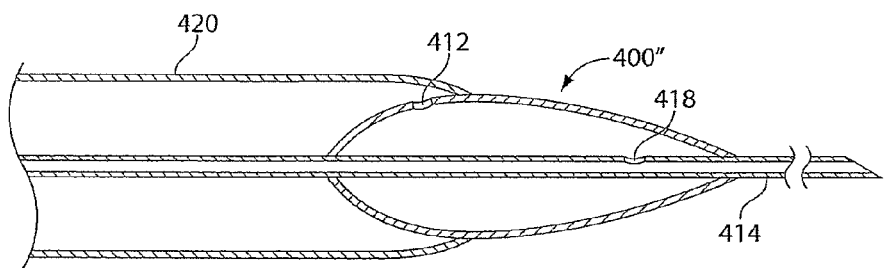

Of course, the positions of apertures 412 and 418 may be varied, so long as they ultimately permit blood to flow from the tip of the needle to the sheath space and/or the sheath sidearm (and, it is preferred, not outside the device). Aperture 412 (or another aperture in addition to aperture 412) may be positioned on the spine 408. Needle aperture 418 may be positioned 0.5 centimeter or more from the dilator end, or proximal to the dilator tip, or proximal to the transition from tube (or bullet) to conical tip. Dilator aperture 412 may be positioned within the bullet just proximal to the needle aperture 418 (FIG. 15). Alternatively, needle aperture 418 and dilator aperture 412 positioned in the spine can be aligned with one another (not shown).

Figure 13D:
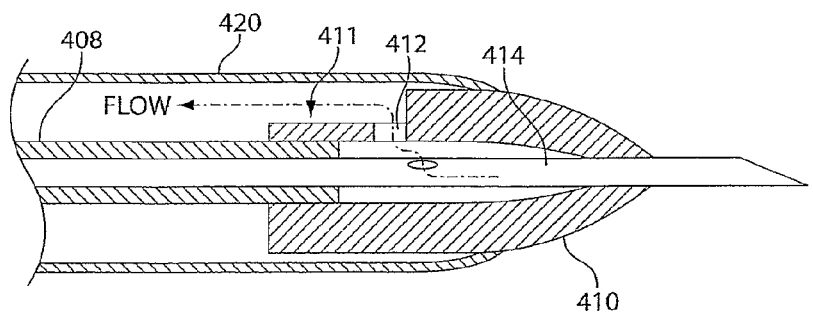
FIGS. 13D-E depict another embodiment of a dilator.
Figure 13E:
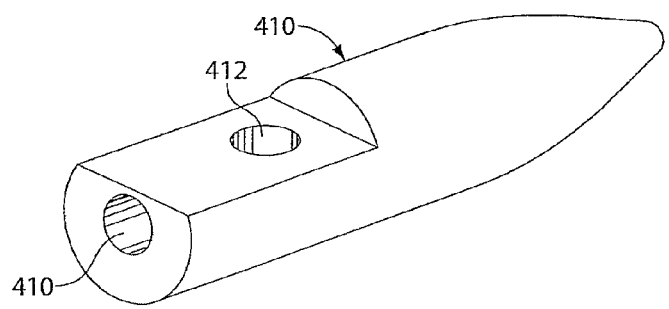

As shown in FIGS. 13D-E, the bullet 410 can include a recessed portion 411. The recessed portion contributes to the space between the dilator and sheath and therefore effectively increases the space between the bullet and the inner diameter of the sheath. This permits higher blood flow and can facilitate visualization. The benefit can be further enhanced by positioning aperture 412 in the recessed portion 411. FIGS. 13D-E also depict the bullet 410 as a separate piece mounted on spine 408 at mounting aperture 409. Alternatively, the bullet and spine can be integrally formed.

Figure 14:
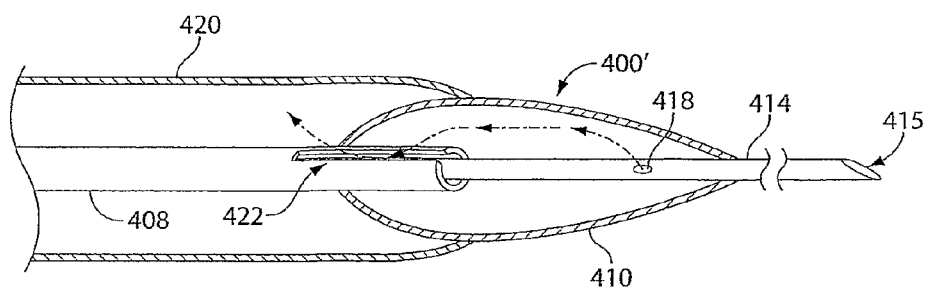
FIGS. 14-16 depict additional embodiments of needle-dilator-sheath assemblies.

FIG. 14 depicts another embodiment of a needle-dilator-sheath assembly, in which the dilator aperture 412 is omitted. Instead, a channel 422 is so formed in the distal end of the spine 408 that it extends from inside the bullet 410' to the sheath space. In this embodiment, blood entering the needle tip 415 can flow into the bullet through needle aperture 418, into the bullet, through the channel, and into the sheath space.

Figure 16:
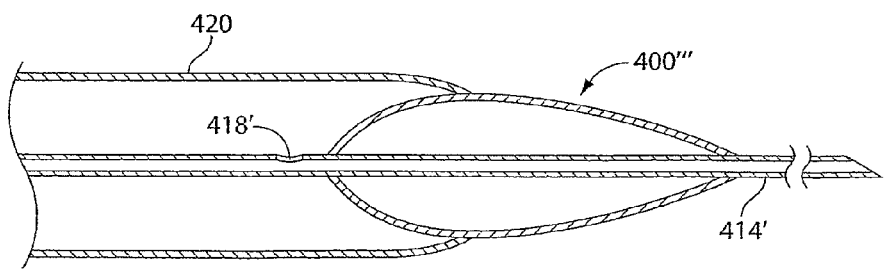

FIGS. 15 and 16 depict still further embodiments in which the dilator spine (and, consequently, the dilator hub) are omitted. Instead, a bullet 400" (FIG. 15) or 400''' (FIG. 16) is attached directly to the needle 414 or 414', respectively. With the FIG. 15 embodiment, blood entering the needle tip flows through aperture 418 into the bullet and through aperture 412 into the sheath space. With the FIG. 16 embodiment, blood flows down the needle 414' to aperture 418' and directly into the sheath space. The bullet may be solid or hollow. When using either of these embodiments, the needle may be inserted fully into the vein either by spinning it 180 degrees (described above) or blunting the needle with the guidewire, with a stylet, or with a sleeve external to the needle tip. These embodiments provide a high optical path length for blood visualization and may be particularly well suited for especially small device sizes, such as 4 French and below, because a constant diameter dilator tube or spine may occupy too much of the sheath space to permit a readily visualizable blood flash.

FIGS. 17-20 depict various views of a hub assembly 500 for a vascular access device. The hub assembly may include a needle hub 502, a dilator hub 520, and a sheath hub 540. The depicted needle hub includes finger grips 504 and 508, which may be provided with depressions 510 and ridges 512 to improve grippability. The needle hub may be hollow. The grips may be separated from one another in a rest condition by a distance d, so that the grips may be squeezed together and thereby change the shape of the needle hub (to be described in more detail shortly). The grips 504, 508 may each extend like arms from a distal hinge portion 514 and contribute respective halves 515 and 516 to the distal shaft of the needle hub. A hollow needle (not shown) may be affixed to the needle hub in the distal portion 514. The distal portion 514 of the needle hub may be received in a chamber 528 of the dilator hub 520. The needle hub may include one or markings, such as a dot, to indicate the orientation of the needle tip bevel to aid the user in positioning the needle for puncture. The needle hub also includes a mating feature 518, such as a ridge (shown) or a depression (not shown) that coordinates with a complementary feature 530 on the proximal part of the dilator hub. By this arrangement, the needle hub is held to the dilator hub through the interaction of the mating features. When the grips are squeezed toward one another, the needle hub's mating feature 518 is so compressed that it clears the dilator hub's mating feature 530, and the needle hub is thereby released from the dilator hub. This may best be appreciated in FIG. 19. The dilator hub, still connected to the sheath, may then be advanced as a unit over the needle into the blood vessel to be accessed. In addition, the needle hub could be moved into the dilator hub, so that mating feature 518 engages recess 519 to clamp the needle hub onto the guidewire and thereby provide a safe starting/shipping configuration. (Alternatively, the needle can be advanced with the dilator and sheath and rotated 180 degrees in the vessel for safety, as described above.)

Mating feature 530 may be a hole, as shown in the figures. This additionally provides a rotational lock to help ensure that the needle bevel is correctly oriented. The post/hole configuration also can allow the operator to remove the needle hub and reinsert it at 180 degrees to the original orientation. This can help left-handed users or facilitate positioning the device for procedures in which space or anatomical constraints favor this orientation. Alternatively, feature 530 can be a groove, to provide rotational freedom where that is more desired or appropriate, such as reorienting the sideport compared to its orientation in the package.

The depicted dilator hub 520 has a distal portion 534 in which a dilator (not shown) may be attached. The distal portion of the dilator hub also has a distal mating feature 532 that interacts with a complementary mating feature on the proximal portion of the sheath 540 to keep the dilator engaged with the sheath. The complementary features may together form, for example, a twist-lock feature, so that the dilator is released from the sheath by gripping the dilator (perhaps at depressions 522 and ridges 524) and twisting it relative to the sheath. The mating feature between the dilator and the sheath is described in more detail below.

Figure 20:
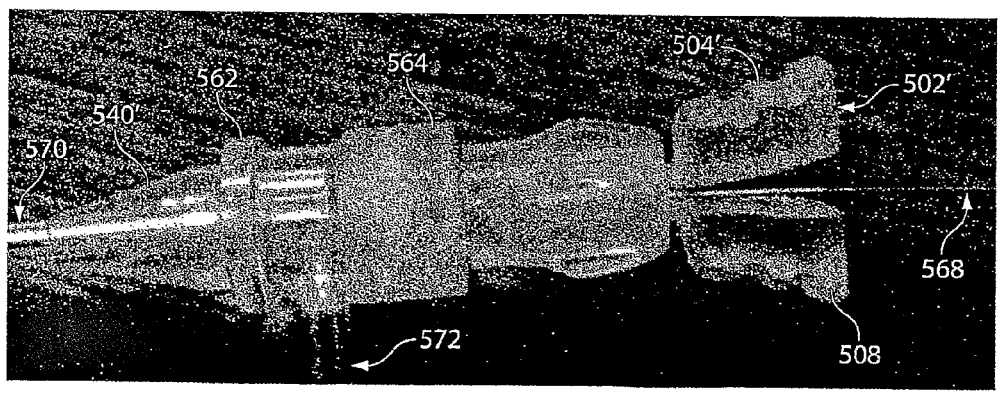
FIG. 20 depicts another embodiment of a needle-dilator-sheath hub assembly.

The sheath 540 includes a main portion 541 and a cap 542, between which is defines a valve space 554. The main portion defines a chamber 558 that can receive the dilator and/or needle and/or guidewire. The main portion may also define a distal channel 560. The sheath may also provide a port 544 for flushing, sampling, etc. The sheath may also include grips, such as depressions 548 and ridges 550 and a suture loop 551. FIG. 20 shows guidewire 568 passing through a channel defined through the device by the needle hub, the dilator hub, and the sheath. The sheath can be a peelaway sheath.

Figure 17:
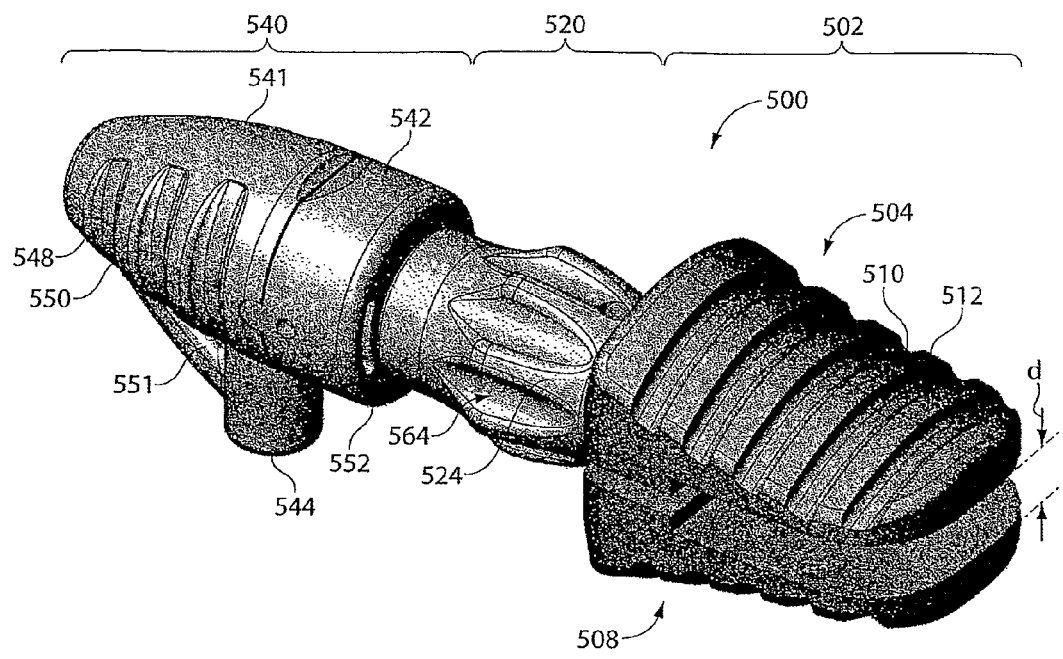
FIG. 17 depicts a hub assembly for a vascular access device.
Figure 18:
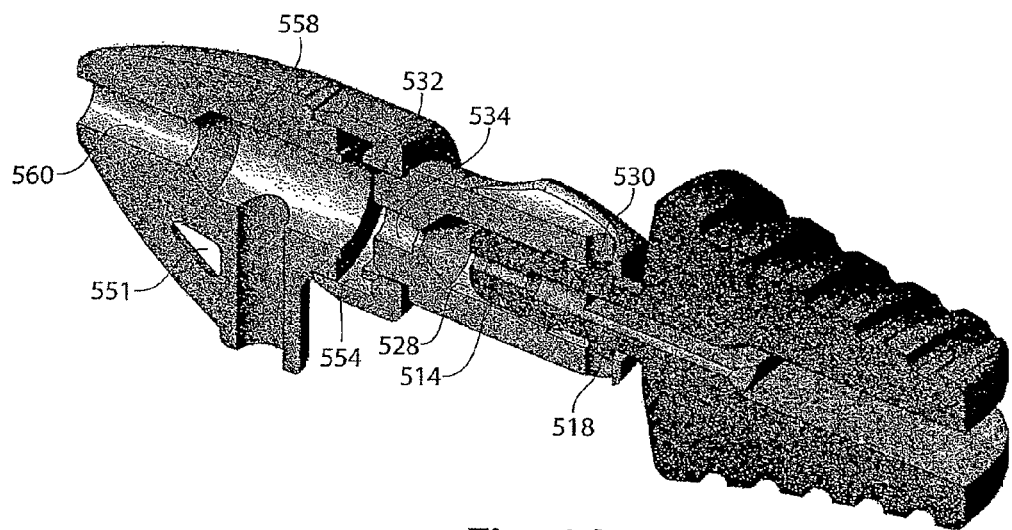
FIG. 18 depicts a perspective longitudinal cross-section of the FIG. 2 embodiment.
Figure 19:
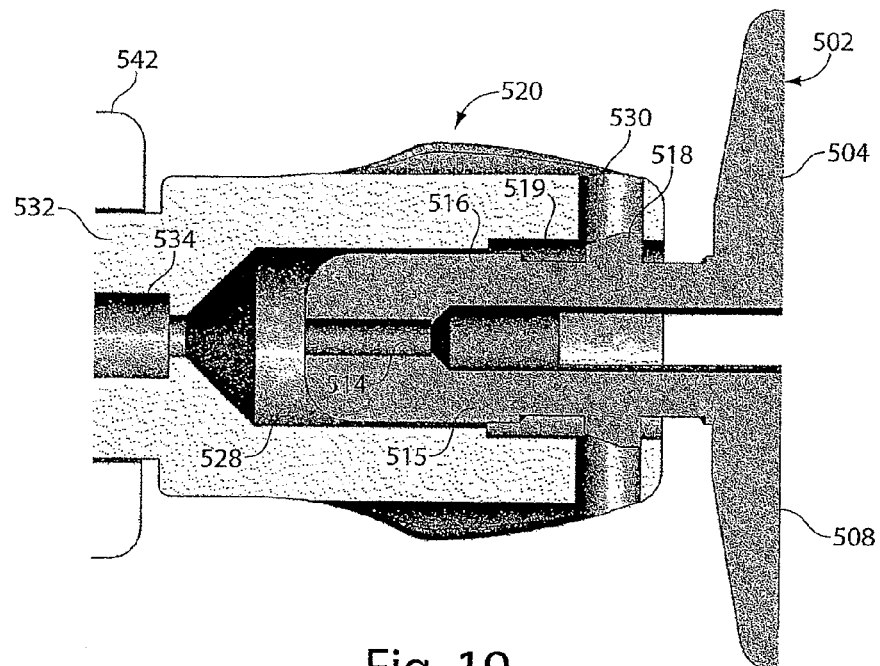
FIG. 19 depicts an elevation longitudinal cross-section of the FIG. 1 embodiment.

FIG. 20 also shows an alternate embodiment with some exemplary modifications. In some embodiments, the outer surfaces of grips 504' and 508' of needle hub 502' can diverge from one another (instead of tapering toward one another as shown in FIG. 17); this may help a user maintain a purchase on the needle hub while urging the dilation/sheath combination forward and/or pulling the needle hub backward. The sheath cap 542 may have one or more slots 564 to provide a spring-like action to allow for the dilator hub to be easily locked or unlocked (described in more detail below). A tube may be attached and/or integrally formed with port 544. Dilator hub 520 may have a rubber seal near its distal end to seal the outer diameter of the needle to the inner diameter of the dilator hub. The seal may be especially useful when the device is used to venous access procedures for the reasons given above. A drop of high-viscosity fluid in the needle may also be included, as described above. The sheath may include a ring 562 or other protuberance for providing a grip surface to hold the sheath in place while the dilator is withdrawn. The sheath main portion may be smooth.

Some exemplary (but not required) dimensions for the embodiment of FIGS. 17-20 are:

needle bore ranging diameter from 25 G to 14 G, preferably 21 G;
exposed needle 3-7 centimeters long (3 cm for central access via radial artery; 5 cm for typical applications; 6 cm for obese patients; 7 cm for femoral access in obese patient);

sheath length 3-15 cm, preferably 5-15 cm, more preferably 5.5 cm or 11 cm;

sheath size 3-10 Fr, preferably 4-8 Fr, more preferably 4 Fr for radial access, or 6 Fr or 7 Fr for subclavian access;

needle aperture 0.5 centimeter or more from dilator end, or proximal to the dilator tip, or proximal to the transition from tube to conical tip;

needle may have second aperture 6 centimeters or less from needle tip.

The sheath may have a radio-opaque tip.

In some embodiments, aspiration, flushing, or air-tightness are necessary (such as central venous catheterization and various procedures in interventional radiology). In such circumstances, it may be important to block off the proximal end of the needle hub where the wire sticks out and is open to atmosphere. Structures for clamping the guidewire in the needle hub are described elsewhere herein, but in some circumstances, the clamp should also provide an air- or liquid-tight seal. One example of such a seal is a Tuohy-Borst ("T-B") valve (an example of a Tuohy-Borst valve is shown in FIG. 8 of U.S. Pat. No. 5,050,606, which is hereby incorporated herein by this reference). A T-B valve or other actuated valve (such as a duckbill-configured valve actuated by an operator) may be included in the needle hub. In use, the valve may be closed before use (the device may be shipped with the valve closed, or the valve may be manually closed before a procedure). This may serve to seal around the guidewire and to hold the guidewire in place. When the vessel is punctured by the needle, the valve may be opened (gently, to avoid jarring the needle tip) to allow advancement of the guidewire. The valve may be left open or may be closed to hold the guidewire in an advanced position.

Figure 20B:
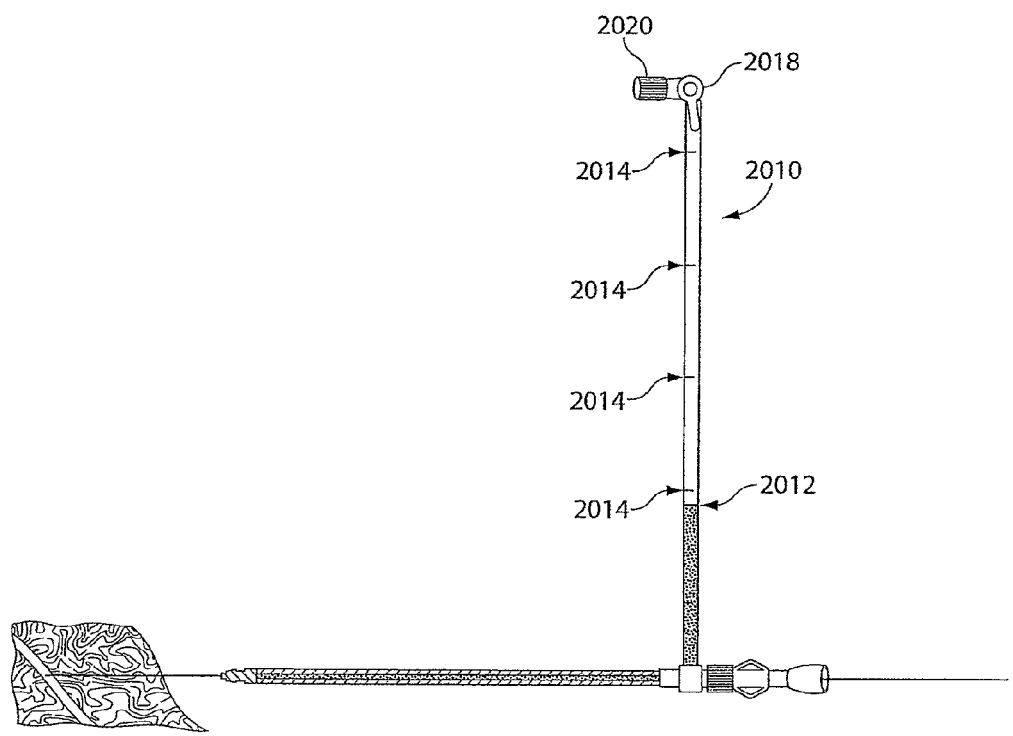
FIGS. 20B-D depict additional features of access devices.

As discussed above, confirmation that access has been obtained in an artery versus a vein may be obtained by observing the color of blood that flows into an access device. However, simple color observation may not serve as sufficient confirmation. A pressure gauge can be used to measure the pressure of back-flowing blood to determine whether it has arterial pressure or venous pressure. A pressure gauge, such as a transducer or column 2010 (FIG. 20B), may be attached to or form part of the side port of an access device described herein. If a column is used, it may be held vertically or at some other angle that includes a vertical component. When the distal end of an access device has gained entry to a blood vessel or other structure with a pressurized liquid, the blood or pressurized liquid may pass through the device and into the column; its height 2012 is indicative of the pressure of the liquid. Comparatively high pressure indicates arterial access, while comparatively low pressure indicates venous access. The measurement of liquid column height may be made by an independent instrument (ruler) or made directly if the side-port column is graduated with markers 2014. The column may include a stopcock 2018 that controls access to a syringe connector 2020.

The side port may be clear, semi-opaque, or translucent to permit visualization of blood or other substance in the side port. In some embodiments, the sheath may be opaque and the side port clear, semi-opaque, or translucent, so that blood or other liquid is not visualized until it enters the side-port.

Figure 20C:
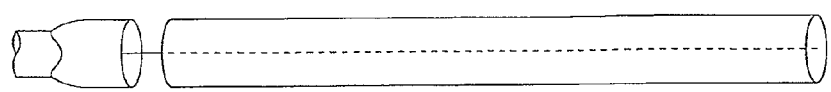
Figure 20D:
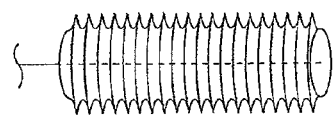

A covering may be placed over all or part of the guidewire, such as over the portion of the guidewire that protrudes or would protrude from the needle hub when the guidewire is loaded in the needle (FIG. 20C). The covering may be flexible to facilitate manual positioning of the guidewire and to preserve its tactile "feel." The covering may provide an airtight or fluid-tight seal of the proximal end of the device, particularly the needle hub. The covering may also protect the sterility of the guidewire. The covering may also prevent the wire from being advanced too far out the distal end of the device (by being attached to the guidewire) or from slipping out or being removed from the proximal end (by being attached to some part of the device). It may also serve to contain spillage of blood or other fluid, especially in the absence of a side port. During use, when the guidewire is advanced, the slack of the covering may "bunch up" around the guidewire (FIG. 20D).

Figure 85:
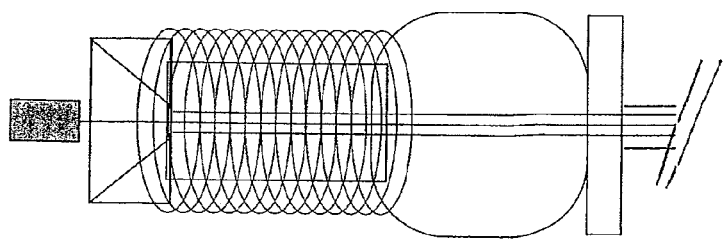
FIGS. 85-87 depict various embodiments of devices having attachments between a needle hub and a dilator hub.
Figure 86:
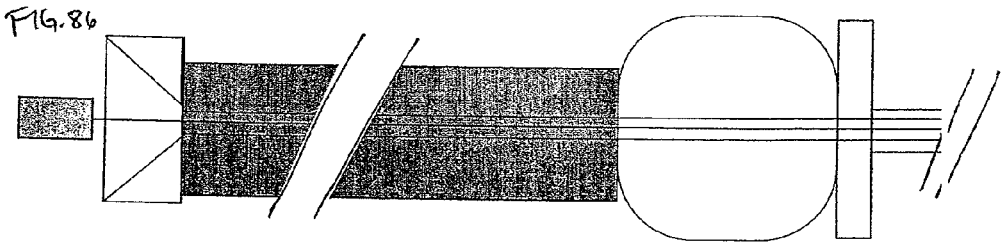
Figure 87:
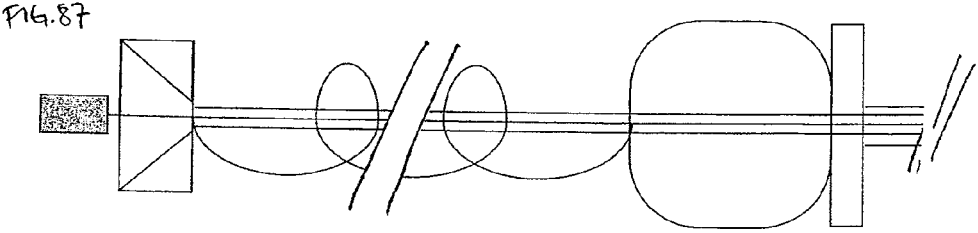

In some embodiments, the dilator hub may be attached (FIG. 85) to the needle hub, such as by a filament (FIG. 87) or by a membrane (FIG. 86) attached to the hubs and surrounding or partially surrounding the needle. This attachment may prevent the needle from being totally retracted from the dilator, thus exposing the sharp needle tip. It may also provide blood containment.

Figure 76:
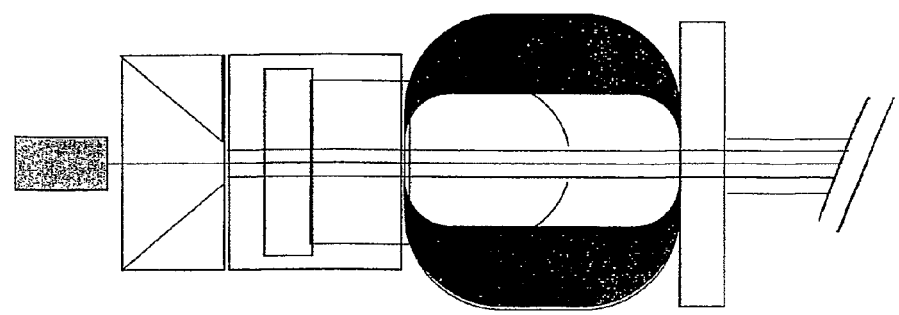
FIGS. 76-79 depict various embodiments and views of devices having trapping mechanisms.
Figure 77:
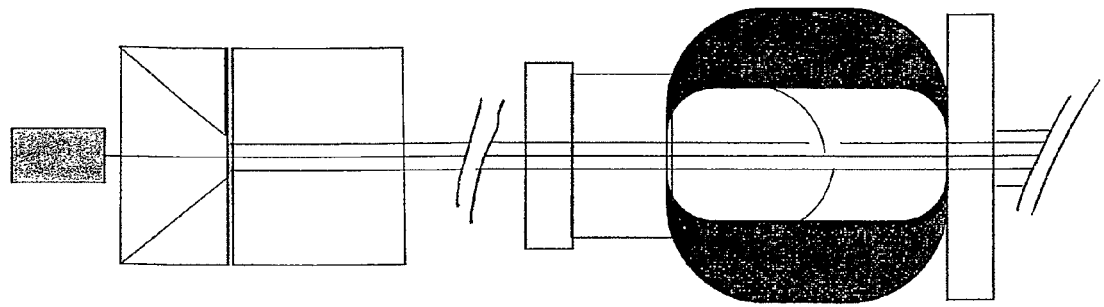
Figure 78:
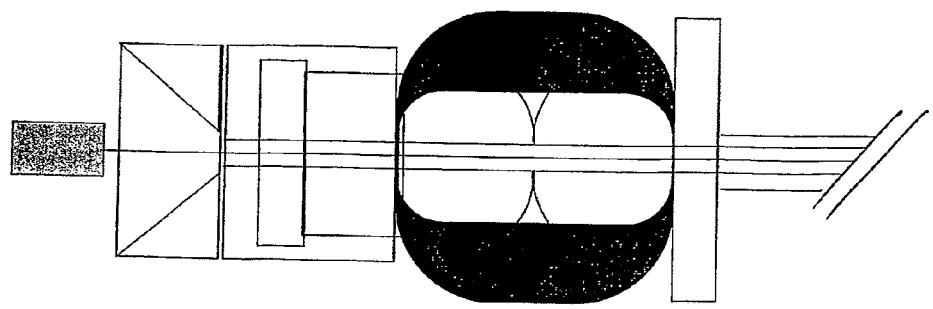
Figure 79:
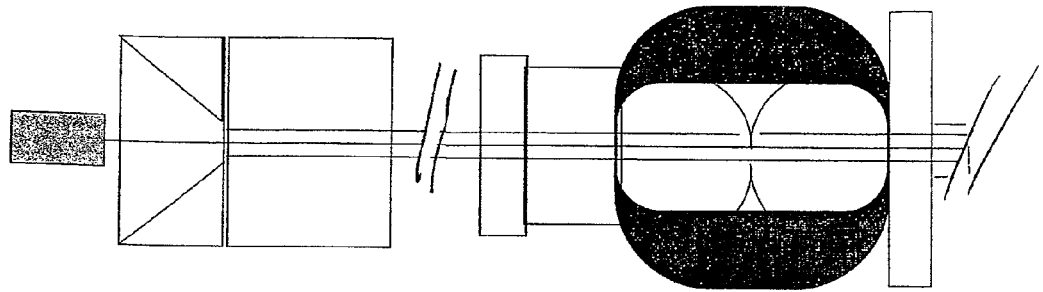

In some embodiments, the dilator hub may interact with the needle depending on their relative positions. One such embodiment includes protrusions from the inner wall of the dilator hub into the lumen. The solid needle cannula can pass between these protrusions in either direction of motion. When the part of the needle cannula interrupted by the side hole passes through the dilator hub, however, the protrusions will catch on the hole. In the example depicted in FIGS. 76-77, the protrusions are directional, that is, they will prevent the dilator and needle from separating, either by advancing the dilator, or equivalently by pulling the needle back. However, they do not prevent the dilator and needle from being pushed back together (either by retracting the dilator or equivalently advancing the needle). In the example depicted in FIGS. 78-79, the protrusions are not directional and once one of them catches on, or protrudes into, the needle side hole, neither sliding the dilator and needle further together, nor separating them further, will be possible.

Figure 80:
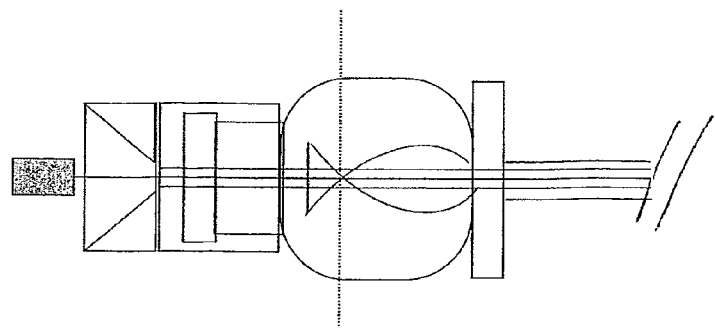
FIGS. 80-84 depict various embodiments and views of devices having blunting mechanisms.
Figure 81:
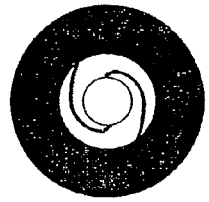
Figure 82:
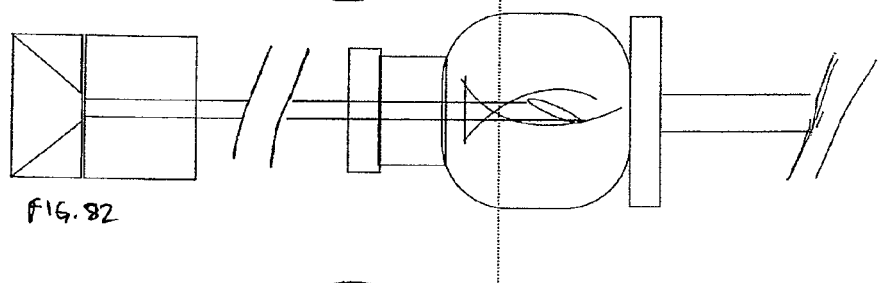
Figure 83:
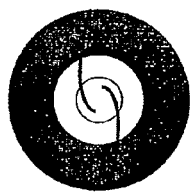
Figure 84:
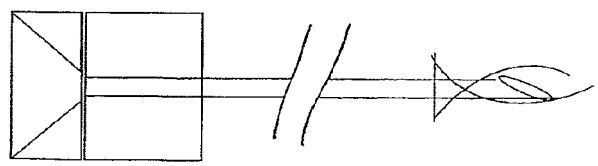

In some embodiments, the dilator hub may include a blunting device that snaps onto the needle distal tip if and when the tip is so retracted as to enter the dilator hub. FIGS. 80-84 illustrate one example. In FIG. 80, the blunting device is held open by the needle shaft. FIG. 81 shows the cross-section indicated in FIG. 80. If the needle is retracted (FIGS. 82-83), the blunting device snaps shut, cradling the needle distal tip. When the needle is fully withdrawn from the device, its tip is protected (FIG. 84).

Figure 21:
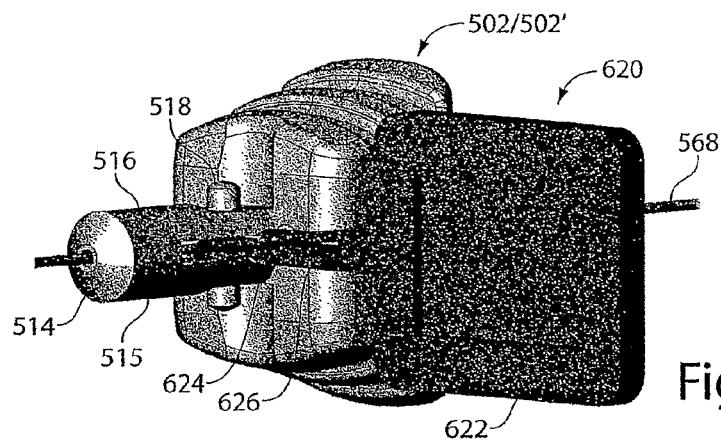
FIGS. 21-27 depict various embodiments of guidewire grabbers or stoppers.
Figure 22:
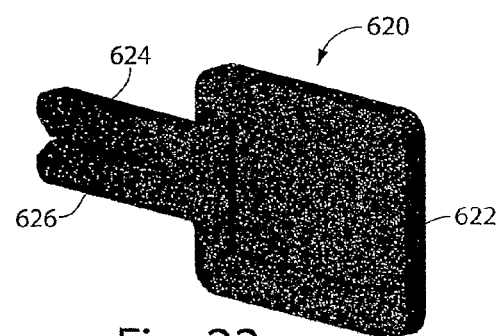

In some embodiments, the device may include a clip or other obstructing piece that can be attached to, for example, the guidewire, to prevent the guidewire from slipping distally while packaged or during introduction of the needle. If not secured, the guidewire may slip past the side aperture in the needle and thereby impede the blood flash or might slip past the needle's bevel tip and effectively blunt it. FIGS. 21-27 show examples of wire grabbers or stoppers. As shown in FIGS. 21-22, a wire grabber 620 can be inserted in the needle hub slot 621 (FIG. 23, also FIGS. 28-29) so that guidewire 568 is held tightly between fingers 624 and 626. When the operator is ready to advance the guidewire, the grabber is removed by pulling tab 622.

Figure 23:
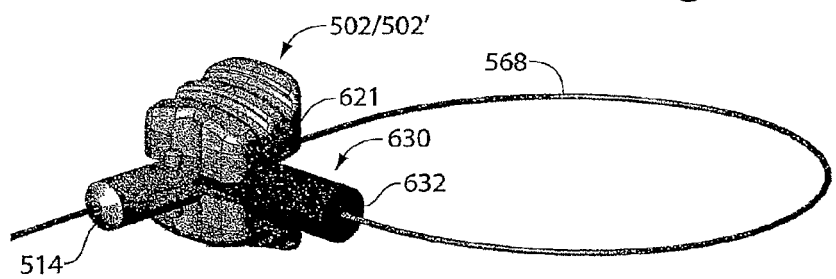
Figure 24:
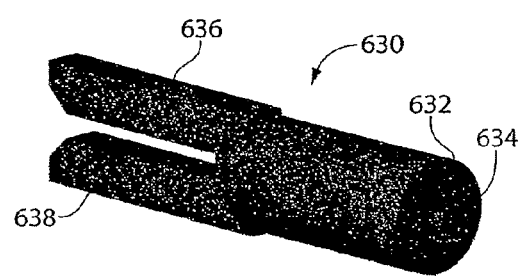
Figure 53:
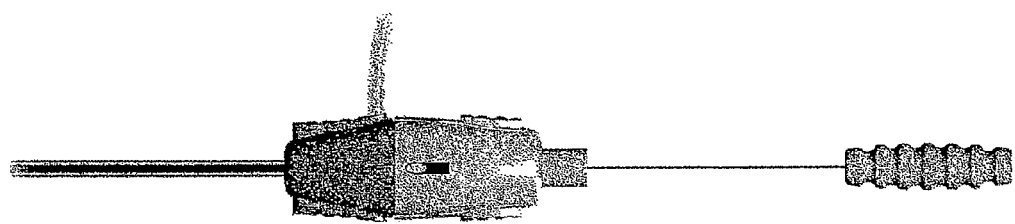
FIGS. 53-58 depict various views and operation of another exemplary embodiment of a needle-dilator-sheath assembly.
Figure 59:
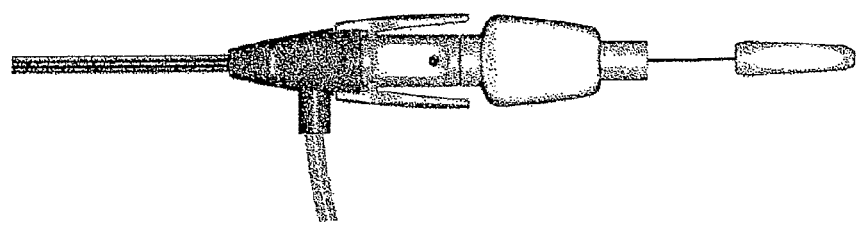
Figure 69:
FIGS. 69-75 depict various views and operation of yet another exemplary embodiment of a needle-dilator-sheath assembly.

Alternatively, the wire stopper 630 shown in FIGS. 23-24 can be used. The stopper similarly has fingers 636 and 638. These extend from a body 632. The proximal end of the guidewire may be affixed to the body 632, such as by being glued in hole 634. This holds the guidewire in a loop and prevents the proximal end of the guidewire from flailing about. When the guide is to be advanced, the stopper is removed. The stopper then can be used as a handle to control the guidewire and/or prevent advancement beyond the needle hub. Other examples of handles/weights are shown in FIGS. 53, 59, and 69. They do not necessarily include structures to grab or stop the guidewire. The guidewire may also include markings at intervals along its length, particularly along its proximal end, to indicate how far the guidewire has been advanced during a procedure.

Figure 24A:
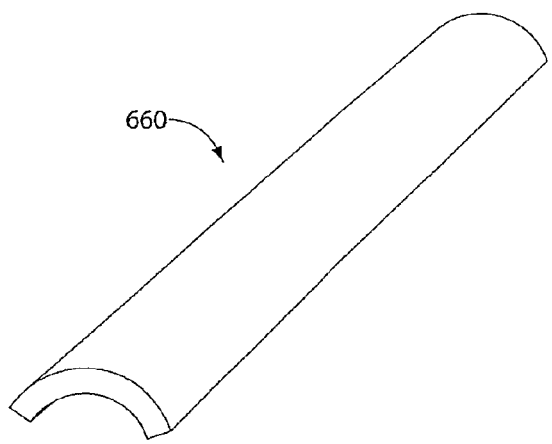
Figure 24B:
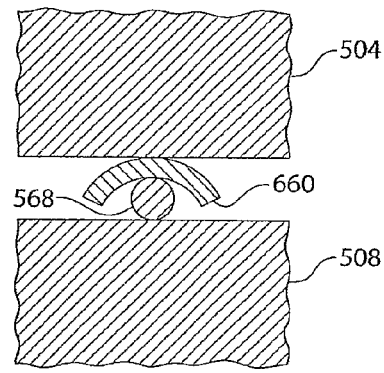
Figure 24C:
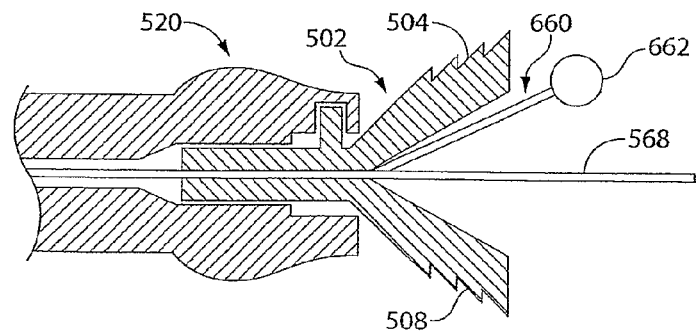

FIGS. 24A-C depict an embodiment of a wedge 660 that may be positioned in the distal orifice of the needle hub 502 against the guidewire to press it in place. In the depicted embodiment, the wedge is an arc-shaped piece, but other shapes are possible, such as round or cornered cross-sections. The wedge can include an enlarged distal portion 662 that provides a surface more easily grasped by a user. A vascular access device can be shipped with the wedge in place to prevent movement of the guidewire during shipment and to prevent movement of the guidewire during the initial steps of gaining vascular access. When the user is ready to advance the guidewire, the wedge can be removed, such as withdrawing from the needle hub by grasping the distal portion.

Figure 25:
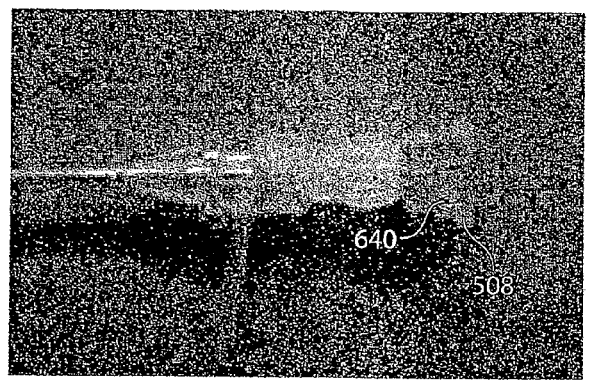
Figure 26:
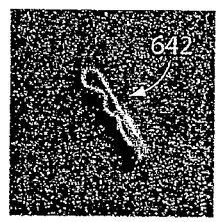
Figure 27:
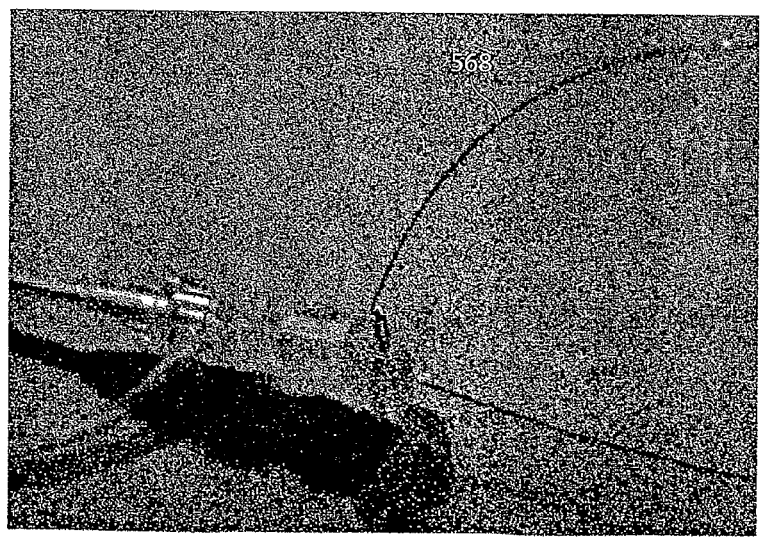

FIGS. 25-27 depict a guidewire locking pin and a device adapted to receive the locking pin. A hole 640 may be formed in the device, such as in grip 508' (depicted) or in another portion of the device. A pin, such as a hitch pin clip 642 may be positioned in the hole such that one arm of the pin goes through the hole and the other presses the guidewire onto the pincer face. The guidewire can optionally be constrained by hooking its proximal end to the pin, as shown in FIG. 27. A retaining mound may be formed in hole 640 complementary to the pin's shape so that the pin fits over this mound and thereby is better retained in the hole.

Figure 28:
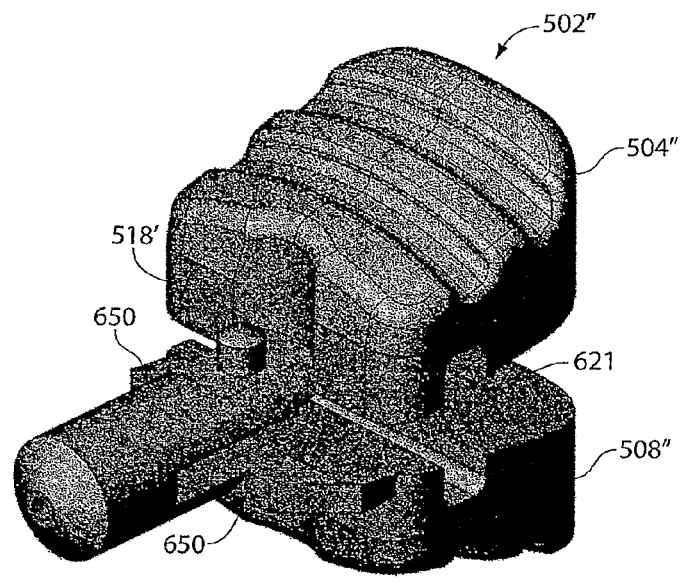
FIGS. 28-32 depict an embodiment of an asymmetric needle hub and a corresponding dilator hub.
Figure 29:
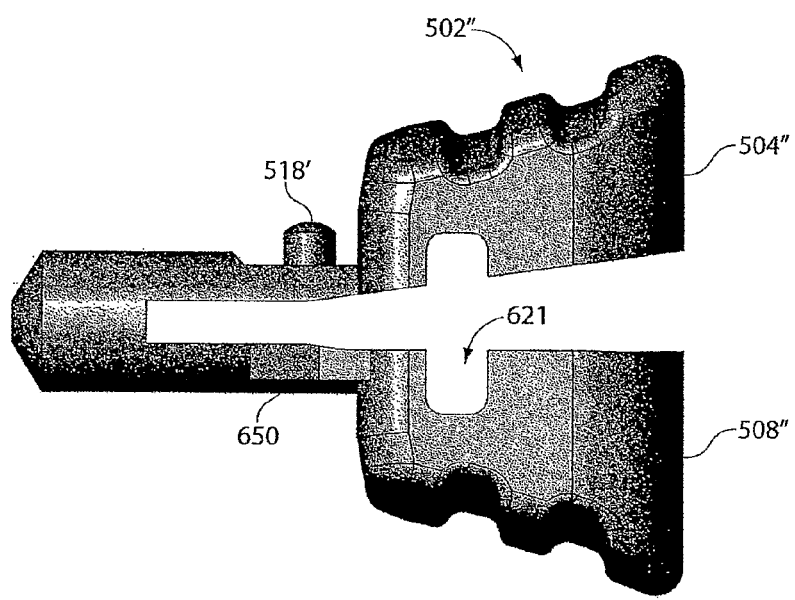
Figure 30:
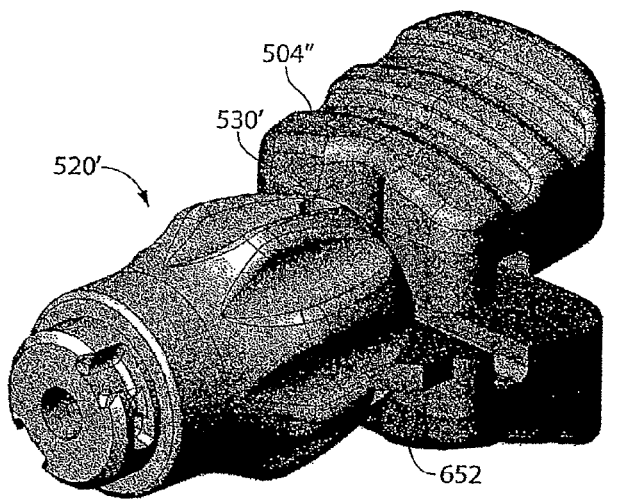
Figure 31:
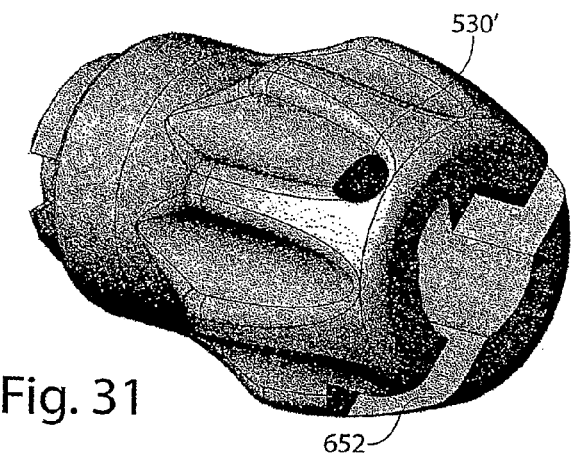
Figure 32:
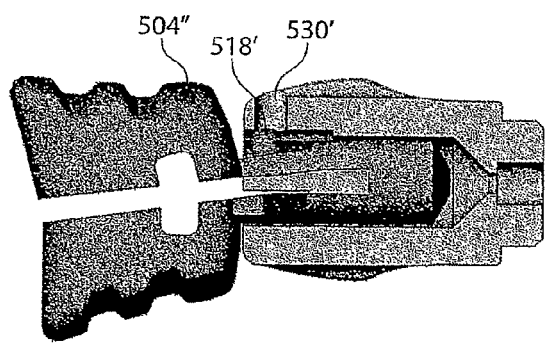

FIGS. 28-32 depict an embodiment of an asymmetrical vascular access hub assembly. FIGS. 28-29 depict the needle hub 502". The hub defines two grips 504" and 508" as before, but only one of the grips (504" in the drawing) is biased. When the grips are pinched, then, grip 504" moves toward grip 508" to clamp the guidewire (FIG. 32 depicts the flexed shape). This arrangement reduces the number of moving parts and can thereby simplify the manufacturing process and relax design tolerances. The needle hub may include a mating feature 518' to mate with a complementary feature 530' in the dilator hub. When the grips are pinched, grip 504" is deformed, causing feature 518' to disengage complementary feature 530'. The feature 518' may be omitted from the unbiased grip 508".

Any of the hub embodiments described herein may also include a fin or fins 650 or pins that engage a complementary slot 652 (FIG. 31) in the dilator hub to prevent rotation before removal of the dilator/sheath assembly from the needle hub.

Figure 32A:
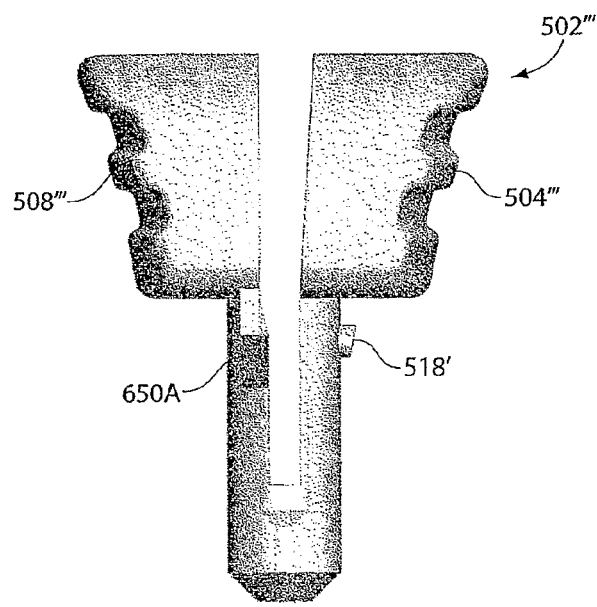
Figure 32B:
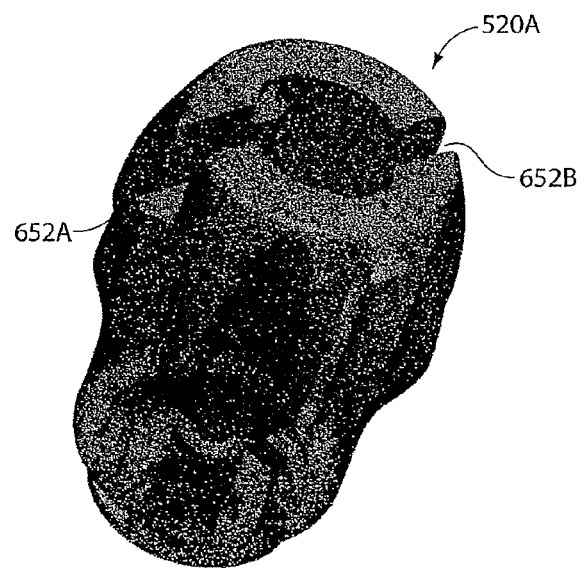

FIGS. 32A-B show additional exemplary embodiments of a needle hub 502''' and dilator hub 520A. The needle hub again may have a single post 518'. In this case, one fin 650a is positioned on one finger grip 508''', and the other fin 650b is on the other grip 504'''. The dilator hub has complementary slots 652A, 652B that line up with the grip-specific fins and do not line up with one another.

Figure 33:
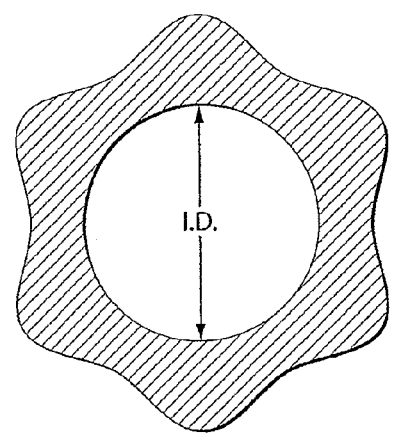
FIGS. 33-34 depict transverse cross-sections of exemplary sheaths.
Figure 34:
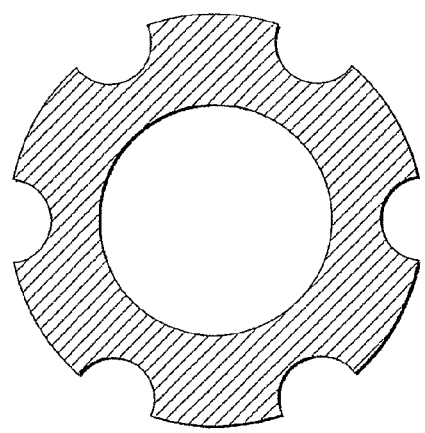

As shown in FIGS. 33-34, the sheath tubing may be formed ridges and/or depressions to improve grip during advancement. A separate component that attaches or clamps reversibly onto the sheath (e.g. from a material such as silicone rubber), in a placement according to the preference of the operator, is another way to improve grip for sheath advancement. Such a component could be included in a kit.

Figure 35:
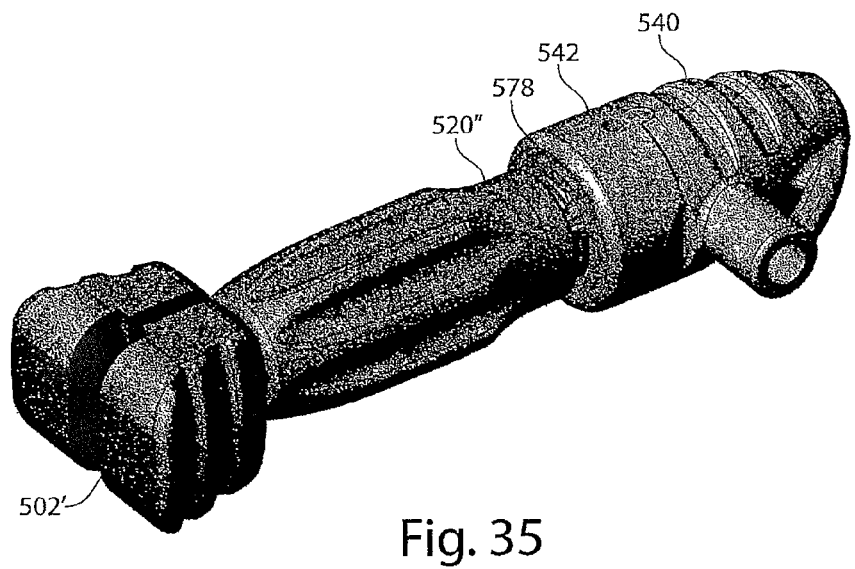
FIG. 35 depicts another embodiment of needle-dilator-sheath hub assemblies.
Figure 36:
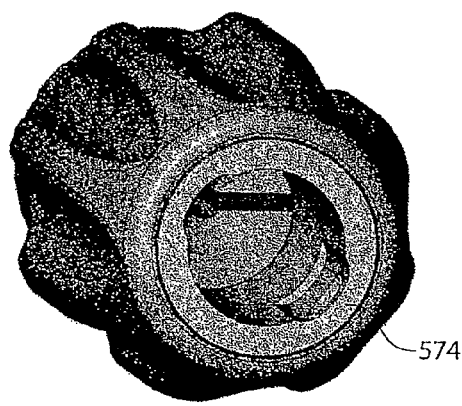
FIGS. 36-39 depict various components of the FIG. 21 embodiment.
Figure 37:
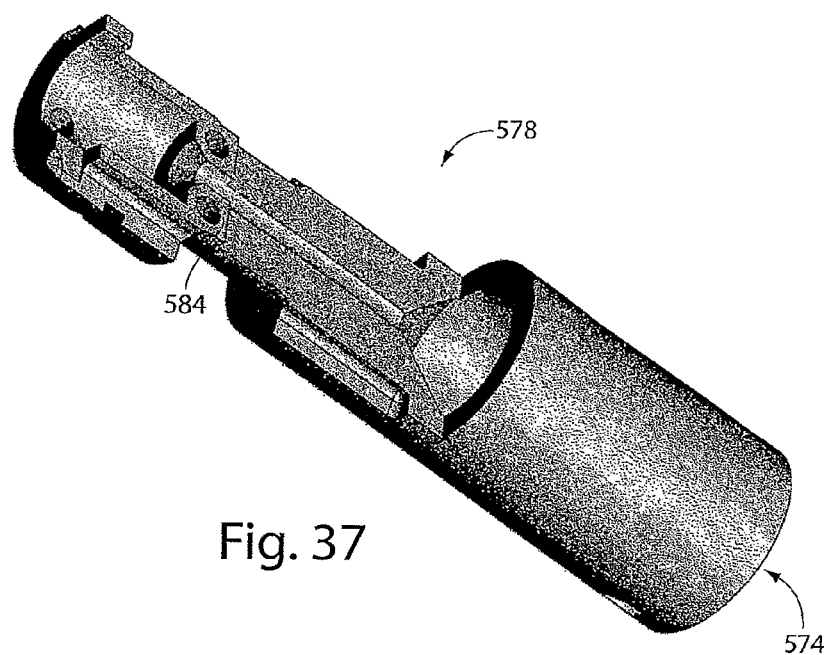
Figure 38:
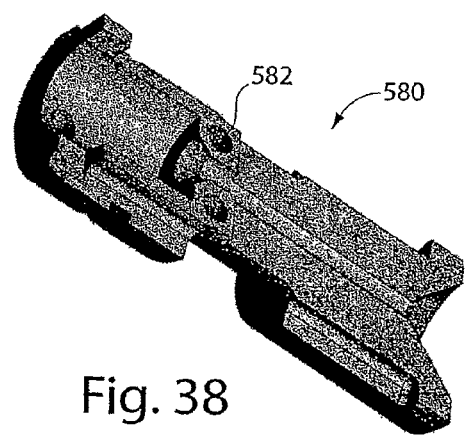
Figure 39:
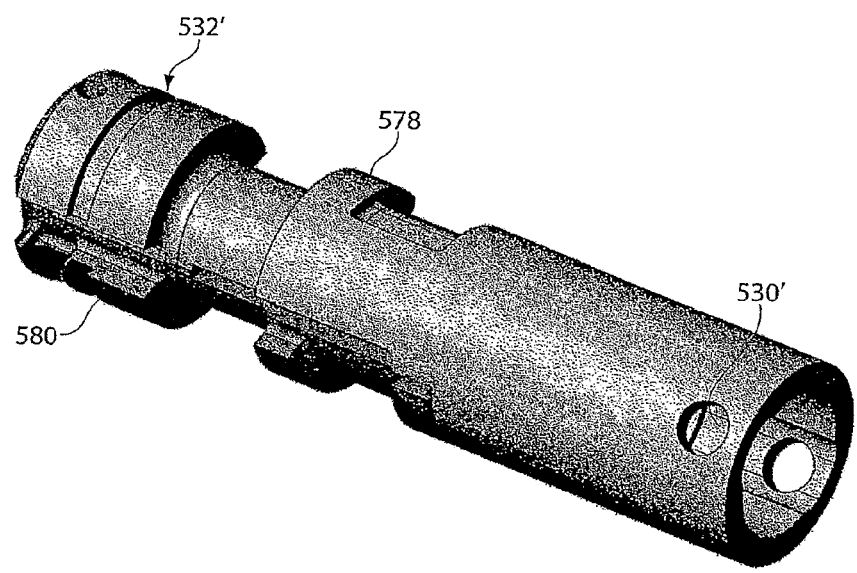
Figure 40:
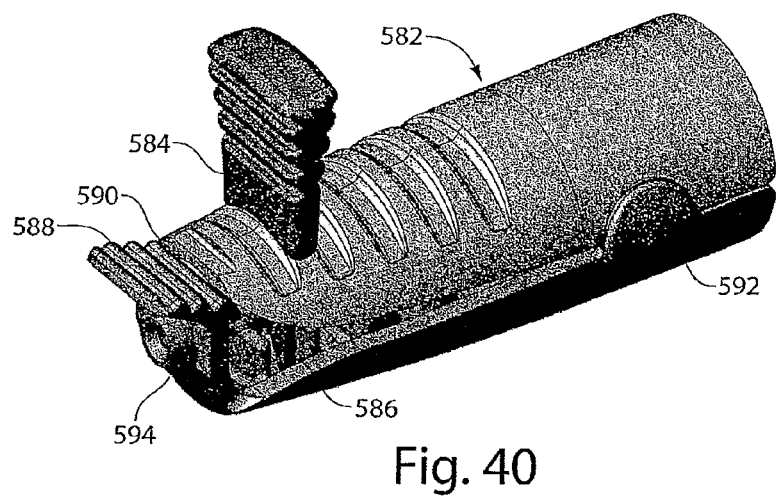
FIGS. 40-43 depict various views of another embodiment of a needle-dilator-sheath hub assembly.
Figure 41:
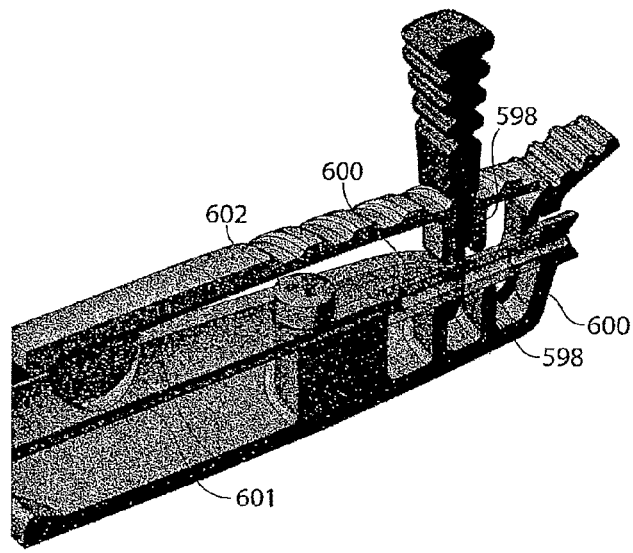
Figure 42:
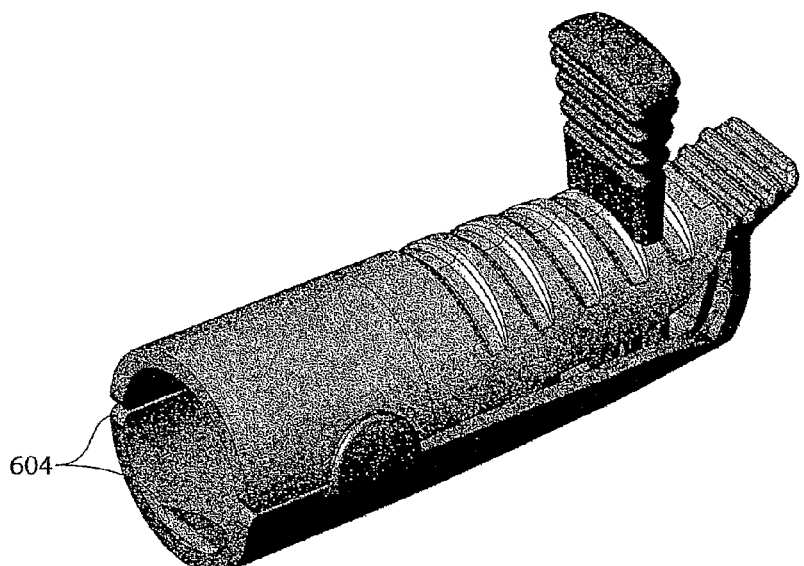
Figure 43:
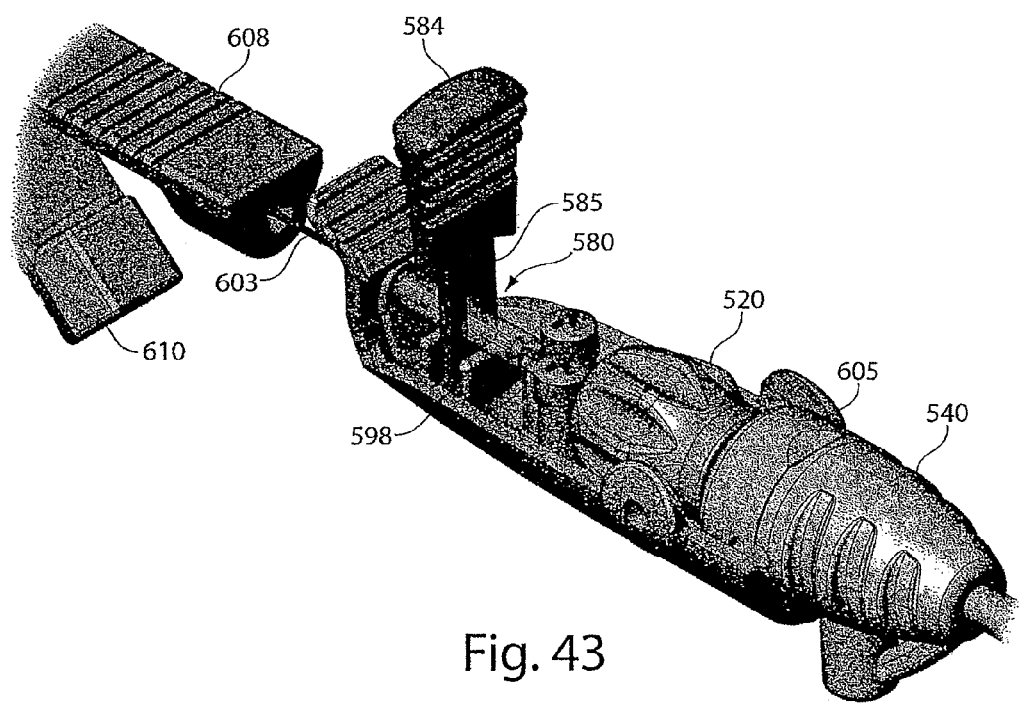
Figure 44:
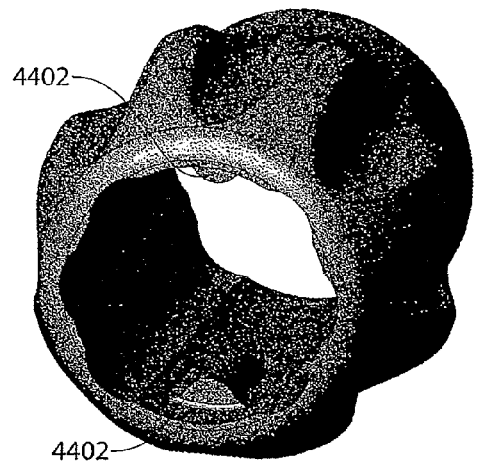
FIGS. 44-48 depict various component of an exemplary dilator hub.
Figure 45:
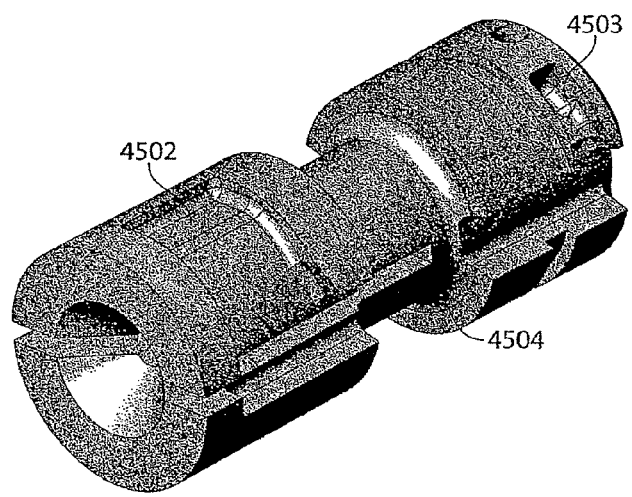
Figure 46:
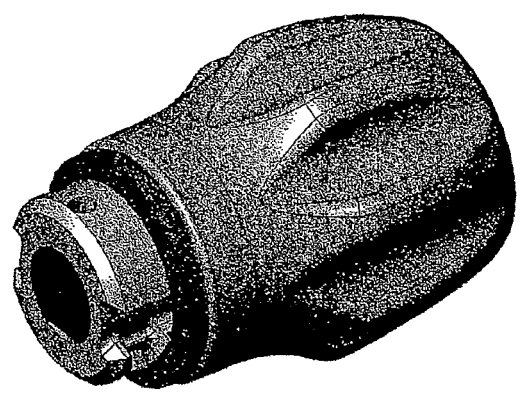

FIG. 35 shows yet another embodiment of a hub assembly, and FIGS. 36-39 show various portions thereof. This depicted embodiment includes sheath 540 and needle hub 502' as previously described. Dilator hub 520" includes an insert 574 inside the dilator that allows the dilator hub to interface with the needle hub and the sheath. The insert includes a proximal end (shown in FIG. 36) that may include mating feature 530' (FIG. 39) as described above for mating feature 530. Insert 574 can be made from a single piece (not shown) or from multiple pieces, such as major piece 578 (FIG. 37) and minor piece 580 (FIG. 28). The major and minor pieces can be fitted together in a variety of ways, such as by aligning receptacles 582, 582 to receive bridging dowels. The insert may include a distal interface feature 532', such as the depicted recess, that interfaces with a complementary interface feature on the sheath (shown, for example, in FIG. 35).

The embodiments of FIGS. 17-39 are used as follows: the needle is introduced into the blood vessel. A blood flash may be observed. A guidewire stopper, grabber, clip, or wedge, if present, can be removed, thereby freeing the guidewire for distal advancement. The guidewire is advanced into the needle and into the blood vessel. The guidewire thereby protects the needle tip and helps to prevent trauma during later manipulation. The needle hub grips are squeezed, thereby levering the proximal portion of the needle hub to clamp on and restrain the guidewire, while the distal portion of the needle hub, via mating feature 518, is freed from dilator hub via mating feature 532. The sheath/dilator hub may then be advanced into the blood vessel. The guidewire can be removed now or at a later stage. At this point, the needle is covered by the dilator and is thereby further protected. The dilator can be then unlocked from the sheath (described in detail with reference to FIGS. 32-37) and withdrawn. The needle remains protected within the dilator, and the two can be removed, optionally with the guidewire, and discarded. This leaves the sheath in place in the blood vessel, ready for use, such as insertion of a catheter.

FIGS. 40-43 depict various views of still another embodiment of a hub assembly. In this embodiment, the needle hub is formed by a clamshell-like assembly 582. A pin 584 may be inserted through an aperture in one shell so that legs 586 straddle a guidewire 603 and restrain it under the bridge 585 of the pin. The guidewire may have a handpiece 608 and/or stopper 610. Needle 601 is fixed in the needle hub, e.g., by bolt or screw 602 or other readily recognized ways.

A silicone tube 600 may surround the guidewire to provide some cushioning. When the device is to be used, the needle is introduced in the blood vessel. The pin is removed, thereby freeing the guidewire to be advanced through the needle. Once the guidewire is positioned, the proximal portions 590 of the clamshell are squeezed together, causing them to rotate at pivot point 592, and they may be held together by tab 588. The squeezing of the proximal portions of the clamshell cause divots 598 to impinge on the guidewire 603 and/or tubing 600, thereby immobilizing the guidewire with respect to the needle hub. At the same time, the pivoting of the clamshell causes retainers 604 on the clamshell to swing clear of corresponding notches 605 on the sheath 540, thereby releasing the dilator hub 520 and sheath 540 to slide with respect to the needle hub 582. The dilator hub/sheath assembly can then be advanced as described previously.

Figure 47:
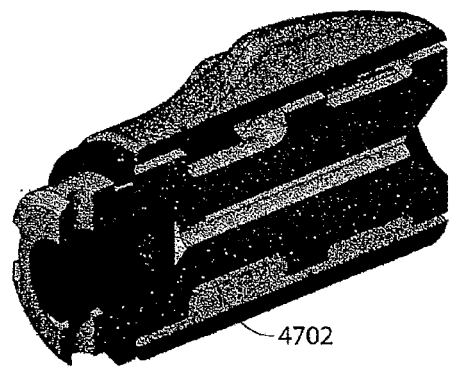
Figure 48:
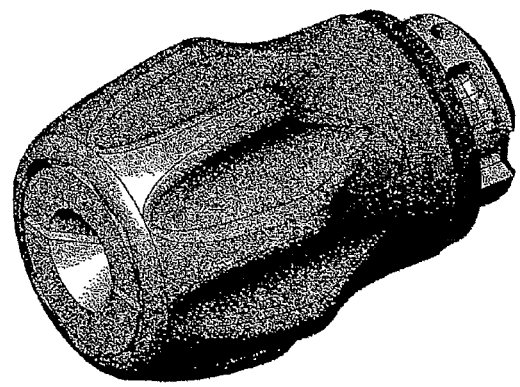
Figure 49:
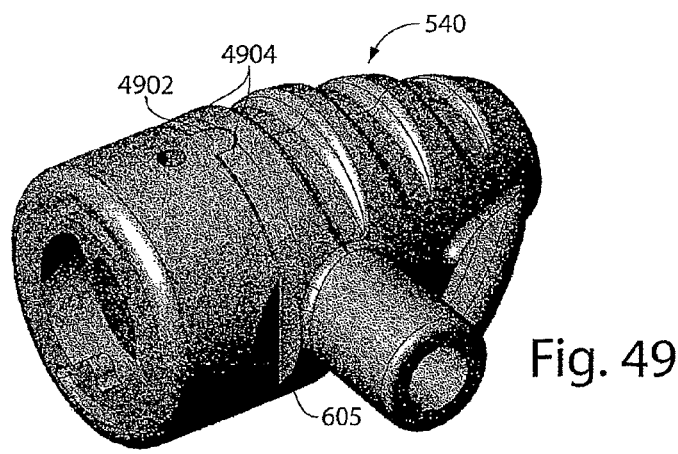
FIGS. 49-51 depict various views of an exemplary sheath.
Figure 50:
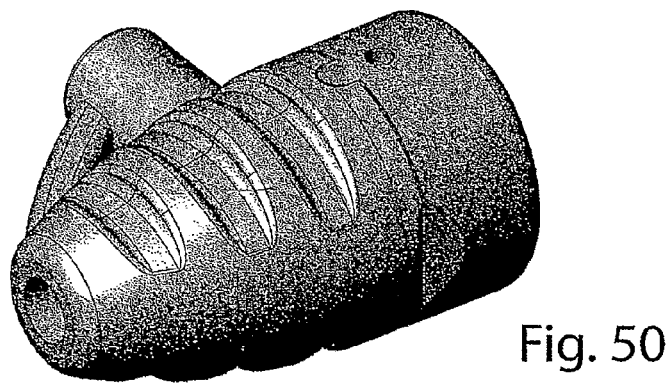

FIGS. 44-48 provide several views of components of another embodiment of a dilator hub assembly. As before, the dilator may include an insert (in this case, a single piece). After the dilator and sheath are advanced, the outer dilator hub piece may be rotated relative to its insert. This causes protrusions 4402 on the inner aspect of the outer dilator hub piece ride into depressions 4502 in the insert, causing the proximal end of the insert to flex at flex point 4504 and compress onto the needle, thereby fixing it in relation to the dilator hub (and thereby trapping the needle tip within the dilator for safety). At the same time, a cam system at the distal end of the dilator hub causes the dilator hub to disengage from the sheath. For example, the distal end of the dilator hub may include a slot 4503 that initially engages a protrusion on the inner surface of the sheath cap; when the dilator hub is rotated, the protrusion is freed from the slot, and the dilator hub can slide off the sheath. As shown in FIG. 47, the dilator hub can include its own seal 4702 to help maintain a fluid and/or gas-tight seal.

Figure 51:
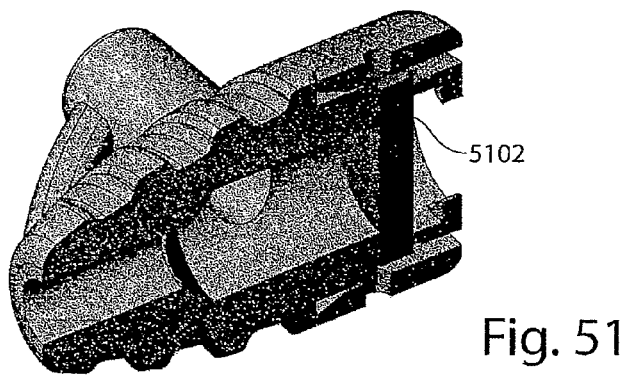
Figure 52:
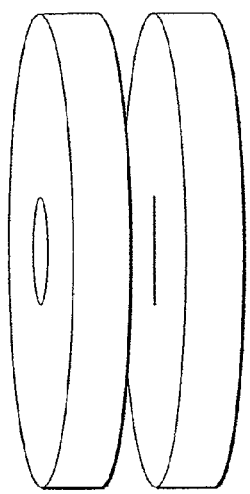
FIG. 52 depicts an exploded view of an exemplary embodiment of a sheath valve.

FIGS. 49-52 show various views and detail of sheath 540. The dilator hub interface can engage the dilator to prevent its release until the dilator is affirmatively disengaged from the sheath as described previously. The valve cap and valve body may include complementary features 4902, 4904 to prevent cap rotation relative to the body. A seal 5102 may be embedded between the valve body and the valve cap. A wide variety of seals may be used, such as those described in U.S. Pat. Nos. 2,022,369, 5,273,546, 4,000,739, 4,424,833, and 4,430,081, each of which is hereby incorporated herein by this reference. An exploded view of one exemplary seal is shown in FIG. 52, in which the seal includes one piece with a hole and a second piece with a slit. A single piece construction may also be desirable where one side incorporates a hole and the other a slit. Such valves may be called "passive" valves because they are not actuated by an operator. A sheath may further or alternately include an actuated valve, such as a Tuohy-Borst valve. The actuated valve can be used to control the effective internal diameter of the sheath (so that devices inserted through the sheath fit snugly) and/or to provide an air- or liquid-tight seal. An actuated valve may be included in a sheath by way of a separate piece that is fitted onto the sheath.

Alternatively, the lumen of the sheath can have a frusto-conical shape or other smooth shape, rather than the transition depicted in FIG. 51.

FIGS. 53-58; 59-68; and 69-75 depict and describe three additional embodiments of needle-dilator-sheath hub assemblies.

Figure 54:
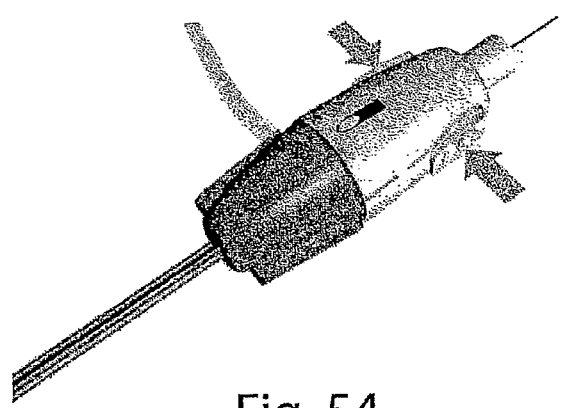
Figure 55:
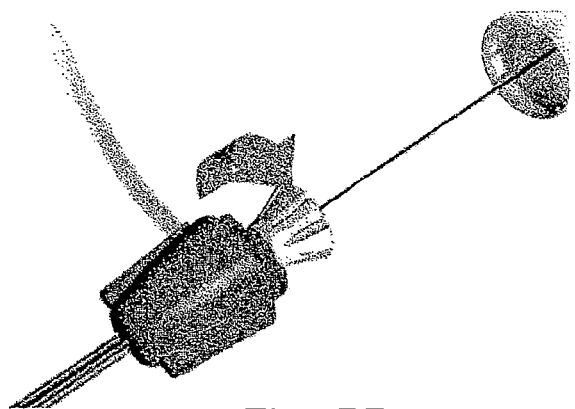
Figure 56:
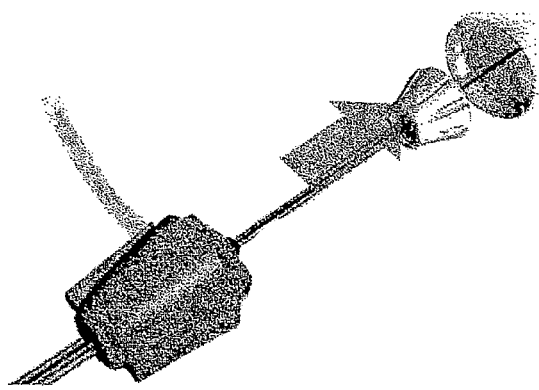
Figure 57:
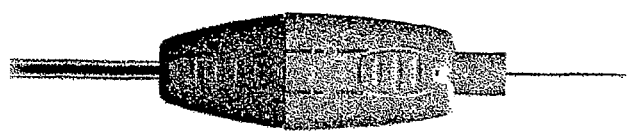
Figure 58:
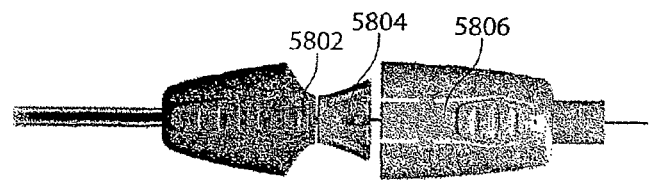

FIG. 53 shows a starting condition of an assembly. In FIG. 54, tabs are squeezed on the needle hub to release the needle hub and allow the dilator and sheath to be advanced. In FIG. 55, the dilator hub is rotated and retracted. In FIG. 56, the dilator, needle, and wire are removed. FIGS. 57-58 provide additional views showing tab latch 5802, drain port 5804, and living hinge tab 5806.

Figure 60:
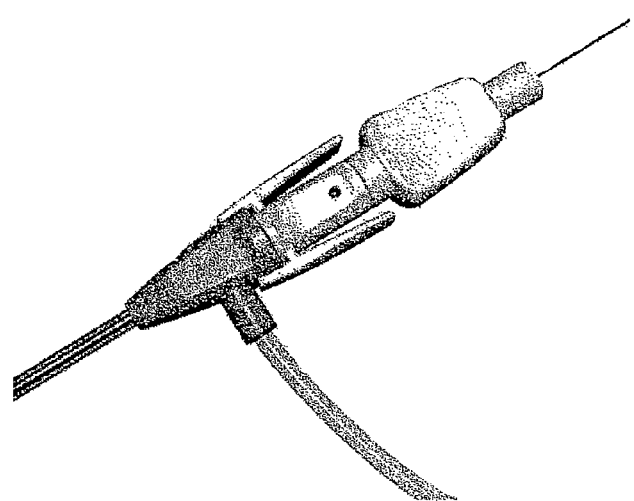
Figure 61:
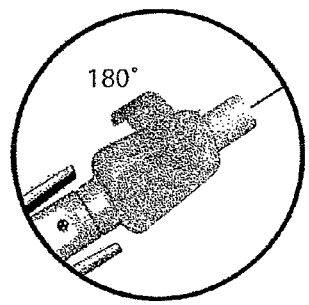
Figure 67:
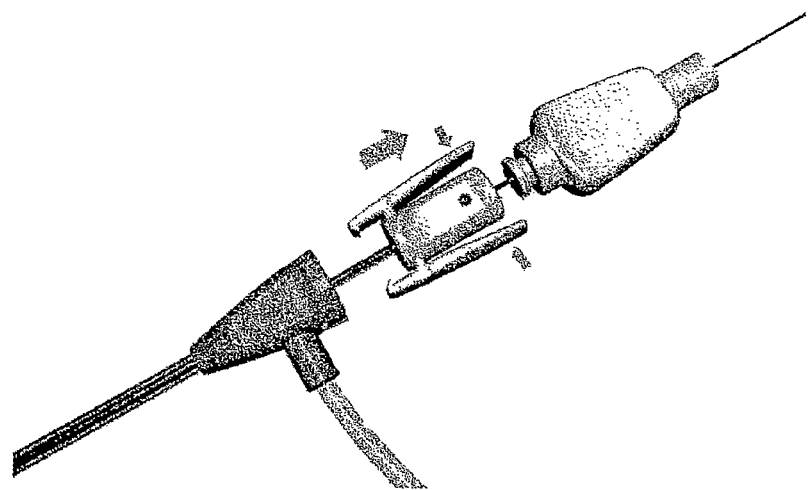
Figure 68:
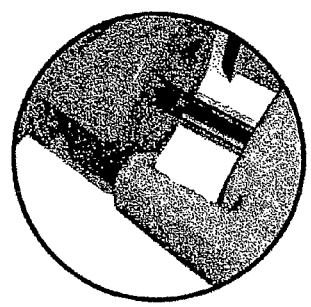

FIGS. 59-60 show a starting condition of another assembly. In FIG. 61, the needle hub is rotatable 180 degrees to orient the needle bevel and unlock the dilator hub. In FIG. 62, the dilator hub and valve body are released from a keyed disk on the needle hub. FIGS. 63-66 show detail of how the dilator hub releases from the needle hub with 180-degree stops. In FIGS. 67-68, tabs are pinched to release the dilator hub from the valve body for removal.

Figure 70:
Figure 71:
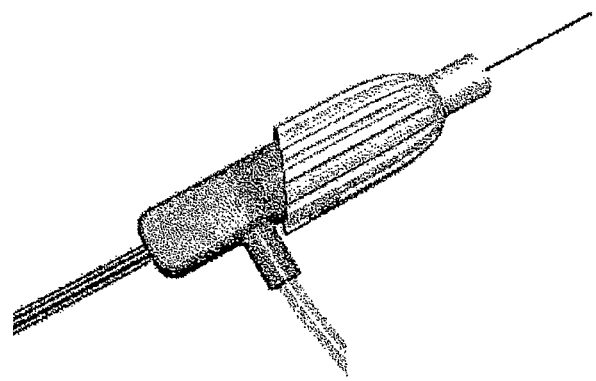
Figure 72:
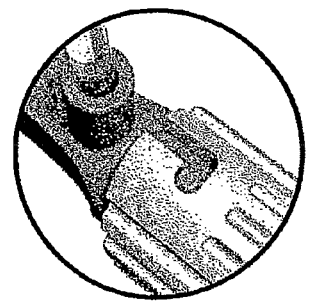
Figure 73:
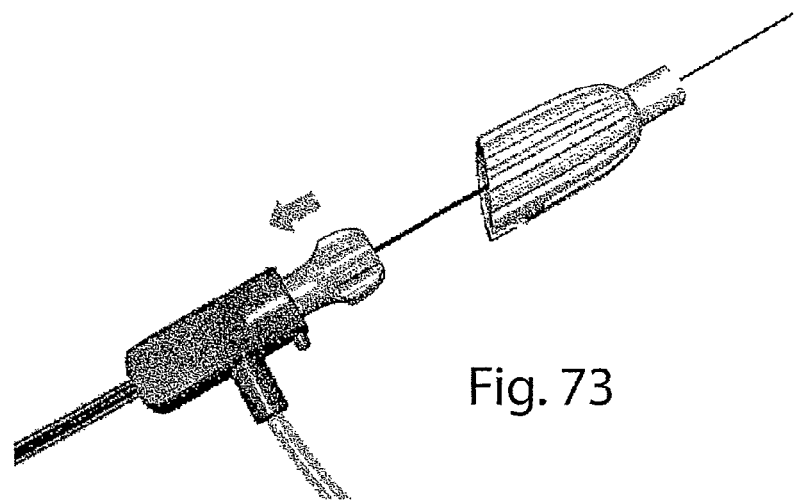
Figure 74:
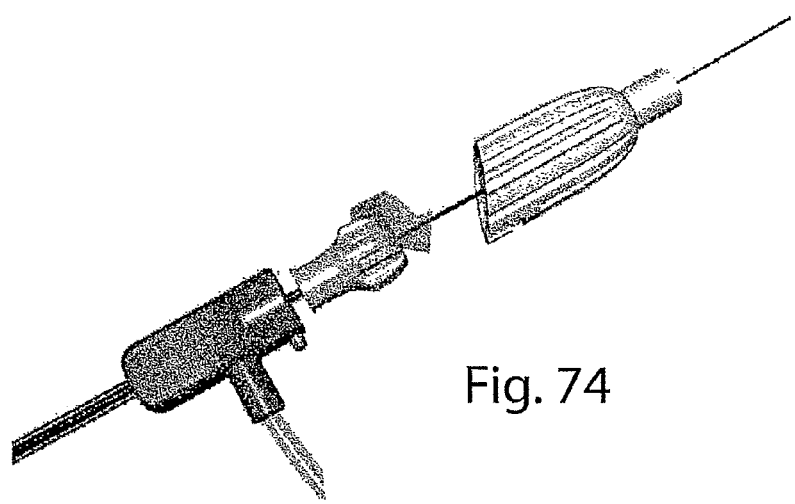
Figure 75:
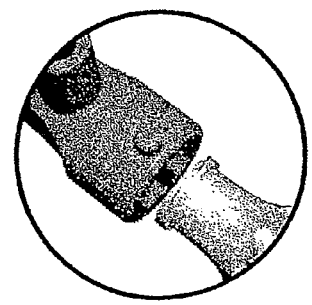

FIG. 69 shows a starting condition of yet another assembly. As shown in FIG. 71, the distal edge of the needle hub is angled to correspond to the needle bevel, thereby providing the practitioner with an indication of needle orientation. In FIG. 72, the needle hub is twisted out of a detent to release it from the dilator hub and valve body. In FIGS. 70 and 73, the dilator hub is revealed as the needle hub is released and the sheath/valve is inserted in the subject. FIGS. 74-75 show twisting of the dilator hub to detach it from the valve body and to allow its removal with the needle and wire.

One embodiment of an access device which may be particularly well-suited for peripherally-inserted central catheterization (PICC) includes a needle hub having no valve and a peelaway sheath with no valve or side port.

The access devices disclosed herein can be used for a wide variety of purposes other than gaining vascular access. For example, the can be used for draining fluid from abscesses, draining air from a pneumothorax, and accessing the peritoneal cavity. Devices used for draining may include side holes in the sheath, such as near the distal end of the sheath.

The disclosed devices may be made from conventional, physiologically acceptable materials. For example, the needle may be made of a rigid polymer or a metal such as stainless steel, nitinol, or the like. The tubes, bullets, sheath, dilator, and/or spine can be made of metals described above and/or suitable polymeric materials such as polyethylene, polypropylene, fluoropolymers and copolymers such as perfluoro (ethylene-propylene) copolymer, polyurethane polymers, PEBAX®, PEEK, Nylon co-polymers and coextrusions. The other elements can be made of the metals described above and/or suitable polymeric materials, such as polyethylene, polycarbonate, ABS, polypropylene, fluoropolymers and copolymers such as perfluoro (ethylene-propylene) copolymer, polyurethane polymers or co-polymers.

Although various features may be depicted in isolation, they may, of course, be combined in various embodiments. For example, a vascular access device may include a hub assembly as shown in FIGS. 17-20 with a bullet dilator such as shown in FIGS. 12-16, and a guidewire stopper, grabber, and/or wedge as shown in FIGS. 21-27. A wide variety of other combinations are possible and readily appreciated.

What is claimed is:

1. A medical device for accessing a body space comprising:
   a hollow needle comprising:
      a needle hub at a proximal end of the needle;
      a needle body extending distally from the needle hub;
      a bore extending through the needle body and the needle hub;
      a side hole extending through a side of the needle body, the side hole being in communication with the bore; and
      a sharpened distal tip;
   a dilator coaxially mounted on the needle, the dilator further comprising:
      a dilator hub at a proximal end of the dilator; and
      a dilator body extending distally from the dilator hub;
   a guidewire preloaded in the needle bore; and
   a blunting device mounted within the dilator hub, the blunting device configured to be held open by the needle body and to snap onto the sharpened distal tip when the sharpened distal tip is retracted into the blunting device, such that the needle can be fully withdrawn from the device with a protected sharpened distal tip.

2. The medical device of claim 1, wherein the dilator at least partially defines a space in communication with the side hole to receive a body fluid.

3. The medical device of claim 2, wherein the dilator comprises at least a translucent portion such that the body fluid in the space can be viewed by a user.

4. The medical device of claim 1, wherein the guidewire is preloaded in a first position to inhibit a flow of body fluid through the bore, the guidewire further being moveable to a second position extending past the side hole.

5. The medical device of claim 4, wherein the guidewire can be advanced so as to cover the needle side hole prior to retraction of the needle distal tip into the blunting device.

6. The medical device of claim 4, wherein the blunting device is held open by the needle body while the guidewire extends beyond the side hole while the needle is being retracted, until the needle distal tip is retracted into the blunting device.

7. The medical device of claim 4, wherein the needle hub comprises actuable grips configured to grasp the guidewire when actuated.

8. The medical device of claim 7, wherein the guidewire can move freely through the needle bore while the grips are not actuated.

9. The medical device of claim 4, wherein the guidewire is inhibited from slipping distally past the side hole while preloaded in the first position.

10. The medical device of claim 1, wherein the medical device comprises a vent in communication with the space in communication with the side hole, allowing the escape of air from the space while hindering the escape of a body fluid.

11. The medical device of claim 10, wherein the vent comprises one or more small openings, pores, or porous material.

12. The medical device of claim 10, wherein the dilator forms at least a portion of the vent.

13. The medical device of claim 1, further comprising a sheath coaxially mounted on the dilator.

14. The medical device of claim 1, wherein the blunting device is fully disposed within the dilator hub.

15. The medical device of claim 1, wherein the needle can be fully withdrawn from the device with the blunting device still closed about the sharpened distal tip to protect the sharpened distal tip.

16. A medical device for accessing a body space comprising:
- a hollow needle comprising:
  - a needle hub at a proximal end of the needle;
  - a needle body extending distally from the needle hub;
  - a bore extending through the needle body and the needle hub;
  - a side hole extending through a side of the needle body, the side hole being in communication with the bore; and
  - a sharpened distal tip;
- a dilator coaxially mounted on the needle, the dilator further comprising:
  - a dilator hub at a proximal end of the dilator; and
  - a dilator body extending distally from the dilator hub;
- a guidewire preloaded in the needle bore; and
- a blunting device fully disposed within the dilator hub, the blunting device configured to be held open by the needle body and to close about the sharpened distal tip when the sharpened distal tip is retracted into the blunting device, such that the needle can be fully withdrawn from the device with a protected sharpened distal tip.

* * * * *